US006953687B1

(12) United States Patent
Rybak et al.

(10) Patent No.: US 6,953,687 B1
(45) Date of Patent: Oct. 11, 2005

(54) VECTORS FOR DELIVERING VIRAL AND ONCOGENIC INHIBITORS

(75) Inventors: Susanna Rybak, Fredrick, MD (US); Andrea Cara, Rockville, MD (US); Gabriele Luca Gusella, Rockville, MD (US); Dianne Newton, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/230,195

(22) PCT Filed: Jul. 17, 1997

(86) PCT No.: PCT/US97/12637

§ 371 (c)(1),
(2), (4) Date: Dec. 10, 1999

(87) PCT Pub. No.: WO98/03669

PCT Pub. Date: Jan. 29, 1998

Related U.S. Application Data

(60) Provisional application No. 60/022,052, filed on Jul. 22, 1997.

(51) Int. Cl.[7] .................. C12N 15/00; C12N 15/63; A01N 63/00; C07H 21/04

(52) U.S. Cl. .................. 435/320.1; 435/455; 424/93.2; 424/93.21; 536/23.5; 536/24.1

(58) Field of Search ............................. 435/320.1, 455; 536/23.5, 24.1; 514/44; 424/93.2, 93.21

(56) References Cited

FOREIGN PATENT DOCUMENTS

EP  0334301 B1  9/1989
EP  0334301 A1  9/1989

OTHER PUBLICATIONS

Poeschia et al.,Development of HIV vectors for anti–HIV gene therapy, Oct. 1996, PROC. NATL. ACAD. SCI., vol. 93 pp. 11395–11399.*
Vile et al, Retroviruses as vectors, 1995, British Medical Bulletin, vol. 51 No. 1 pp. 12–30.*
Verma et al., Gene therapy–promises, problems and prospects, Spt. 1997, Nature, vol. 389 pp. 239–242.*
Crystal, Transfer of genes to humans: Early lessons and obstacles to success, Oct. 1995, Science, vol. 270 pp. 404–410.*
Ding et al., A single amino acid determines the immunostimulatory activity of interleukin Jan. 10, 2000, J. Esp. Med., vol. 191 No. 2, pp. 213–223.*
Deonarain, Ligand–targeted receptor–mediated vectors for gene therapy, 1998, Exp. Opin.Ther. Patent, vol. 8 No. 1 pp. 53–69.*

Eck et al., Goodman & Gilman's The Pharmacological Basis of Therapeutics, 1996, McGraw–Hill, New York, p. 77–101.*
Gorecki, D., 2001, Expert opin. Emerging Drugs, vol. 6, No. 2, p. 187–198.*
Akkina, et al. "High–Efficiency Gene Transfer into CD34[+] Cells with a Human Immunodeficiency Virus Type 1–Based Retroviral Vector Pseudotyped with Vesicular Stomatitis Virus Envelope Glycoprotein G" *J. of Virology* Apr. 1996 vol. 70 (4) pp. 2581–2585.
Bahner, et al. "Comparison of trans–Dominant Inhibitory Mutant Human Immunodeficency Virus Type 1 Genes Expressed by Retroviral Vectors in Human T Lymphocytes" *J. of Virology* Jun. 1993 vol. 67 (6) pp. 3199–3207.
Brenner, Malcom, K. "Gene Transfer into Human Hematopoietic Progenitor Cells: A Review of Current Clinical Protocols" *J. of Hematotherapy* (1993) vol. 2 pp. 7–17.
Chang, et al. "Regulation by HIV Rev Depends upon Recognition of Splice Sites" *Cell* Dec. 1989 vol. 59 pp. 789–795.
D'Agostino, et al. "The Rev Protein of Human Immodeficiency Virus Type 1 Promotes Polysomal Association and Translation of gag/pol and vpu/env mRNAs" *Molecular and Cellular Biology* Mar. 1992 vol. 12 (3) 1375–1386.
Felber, et al. "Rev Protein of Human Immunodeficiency Virus Type 1 Affects the Stability and Transport of the Viral mRNA" *Proc. Natl. Acad. Sci.* Mar. 1989 vol. 86 pp. 1495–1499.
Feinberg, et al. "Intracellular Immunization: Trans–Dominant Mutants of HIV Gene Products as Tools for the Study and Interruption of Viral Replication" *AIDS Research and Human Retroviruses* (1992) vol. 8 (6) pp. 1013–1022.
Ghattas, et al. "The Encephalomyocarditis Virus Internal Ribosome Entry Allows Efficient Coexpression of Two Genes from a Recomb Provirus in Cultured Cells and in Embryos" *Molecular and Cellular Biology* Dec. 1991 vol. 11 pp. 5848–5859.
Hsieh, et al. "Improved Gene Expression by a Modified Bicistronic Retroviral Vector" *Biochemical and Biophysical Research Communication* Sep. 1995 vol. 214 (3) pp. 910–917.
Itoh, et al. "HTLV–1 rex and HIV–1 rev Act Through Similar Mechanisms to Relieve Suppression of Unspliced RNA Expression" *Oncogene* (1989) vol. 4 pp. 1275–1279.
Levine, et al. "Efficient Gene Expression in Mammalian Cells from a Dicistronic Transcriptional Unit in an Improved Retroviral Vector" *Gene* (1991) vol. 108 pp. 167–174.

(Continued)

*Primary Examiner*—Shin–Lin Chen
(74) *Attorney, Agent, or Firm*—Townsend and Townsend and Crew LLP

(57) ABSTRACT

Cell transformation vectors for inhibiting HIV and tumor growth are provided. Optionally, the vectors encode RNAses such as EDN. Cells transduced by the vectors and methods of transforming cells (in vitro and in vivo) using the vectors are also provided.

36 Claims, 8 Drawing Sheets

OTHER PUBLICATIONS

Moore, Malcolm, A.S. "Ex Vivo Expansion and Gene Therapy Using Cord Blood CD34+Cells" *Journal of Hemotherapy* (1993) vol. 2 pp. 221–224.

Nable, et al. "A Molecular Genetic Intervention for AIDS— Effects of a Transdominant Negative for of Rev" *Human Gene Therapy* (1994) vol. 5 pp. 79–80.

Naldini, et al. "In Vivo Gene Delivery and Stable Transduction of Nondividing Cells by a Lentiviral Vector" *Science* Apr. 1996 vol. 272 ppl 263–267.

Poeschla, et al. "Development of HIV Vectors for Anti–HIV Gene Therapy" *Proc. Natl. Acad. Sci.* Oct. 1996 vol. 93 pp. 11395–11399.

Tan, et al. "Inhibitory Activity of the Equine Infectious Anemia Virus Major 5' Splice Site in the Absence of Rev" *J. of Virology* Jun. 1996 vol. 70 (6) pp. 3645–3658.

Thierry, et al. "Systemic Gene Therapy: Biodistribution and Long–term Expression of a Transgene in Mice" *Proc, Natl. Acad. Sci.* Oct. 1995 vol. 92 pp. 9742–9746.

Trono, et al. "HIV–1 Gag Mutants Can Dominantly Interfere with the Replication of the Wild–Type Virus" *Cell* Oct. 1989 vol. 59 pp. 113–120.

Venkatesh, et al. "Selective Induction of Toxicity to Human Cells Expressing Human Immunodefiency Virus Type 1 Tat by a Conditionally Cytotoxic Adenovirus Vector" *Proc. Natl. Acad. Sci.* Nov. 1990 vol. 87 pp. 8746–8750.

Youle, et al. "RNase Inhibition of Human Immunodeficiency Virus Infections of H9 Cells" *Proc. Natl. Acad. Sci.* Jun. 1994 vol. 91 pp. 6012–6016.

Yu, et al. "Progress Towards Gene Therapy for HIV Infection" *Gene Therapy* (1994) vol. 1 pp. 13–26.

Zenke, et al. "Receptor–mediated Endocytosis of Transferrin–polycation Conjugates: An Efficient Way to Introduce DNA into Hematopietic Cells" *Proc. Natl. Acad. Sci.* May 1990 vol. 87 pp. 3655–3659.

* cited by examiner

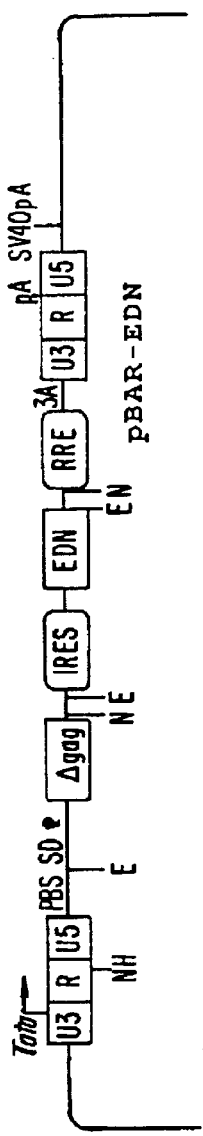

FIG. 4.

IRES
```
ATTCCCCCCC TCTCCCTCCC CCCCCCCTAA CGTTACTGGC CGAAGCCGCT        50
TGGAATAAGG CCGGTGTGCG TTGTCTATAT GTTATTTTCC ACCATATTGC       100
CGTCTTTTGG CAATGTGAGG GCCCGGAAAC CTGGCCCTGT CTTCTTGACG       150
AGCATTCCTA GGGGTCTTTC CCCTCTCGCC AAAGGAATGC AAGGTCTGTT       200
GAATGTCGTG AAGGAAGCAG TTCCTCTGGA YCTTCTTGA AGACAAACAA        250
CGTCTGTAGC GACCCTTTGC AGGCAGCGGA ACCCCCCACC TGGCGACAGG       300
TGCCCTCGCG YYCAAAAGCC ACGTGTATAA GATACAGGTG CAAAGGCGCC       350
ACAACCCCAG TGCCACGTTG TGAGTTGGAT AGTTGTGGAA AGAGTCAAAT       400
GGCTCTCCTC AAGCGTATTC AACAAGGGGC TGAAGGATGC CCAGAAGGTA       450
CCCCATTGTA TGGGATCTGA TTTGGGCCCT CGGTGCACAT GCTTTACATG       500
TGTTTAGTCG AGGTTAAAAA ACGTCTAGGC CCCCCGAACC ACGGGGACGA       550
GGTTTTTCCT TTGAAAAACA CGATGATAAG CTTGCCAC                   588
```

INTERVENING SEQUENCE
CTAGAAATAATTTGTTTAACTTTAAGAAGGAGATATACATATG

EDN
```
AAA CCG CCG CAG TTC ACT TGG GCT CAG TTC GAA ACT TAC CAT ATC AAC ATG ACT TCT        60
CAG CAG TGC ACT AAC GCT ATG CAG GTT CAG AAC AAC TAC CAG CGT CGT TGC AAA AAC CAG   120
AAC ACT TTC CTG ACT CTG CTG ACT TTC GCT AAC GTT GCT AAC GTT TGC GGT TCT CAG AAC CCG AAC ATG   180
ACT TGC CCG TCT AAC AAA ACT CGT AAG AAC TGC CAC AAC ATC CAG CGT TCT TCT AAC TGC CGT TAC CGT CCG CAG   240
ATC CAT CTG TGC AAC CTG ACT ATG TTC TAC ATC CCG CCG TGC GTT GCT GAC CGT TGC GAC CAG CGT CGT GCT CAG   300
ACT CCG CAG GCT AAC ATG TTC TAC ATC CAT CTG GAC CGT CGT ATC                                         360
CCG CAG TAC CCG CAG GTT GTT CCG CAG TAC CTT CAT CTG GAC CGT ATC ATC                                 402
```

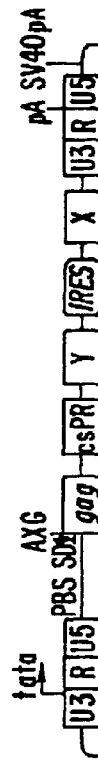
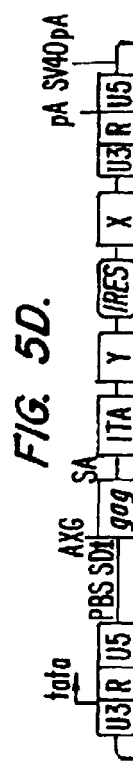
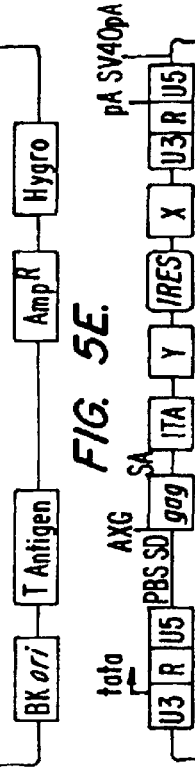
FIG. 5D.  FIG. 5E.  FIG. 5F.
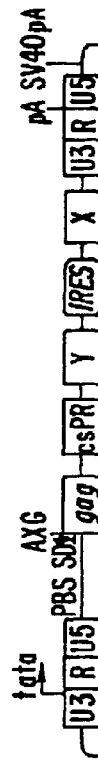
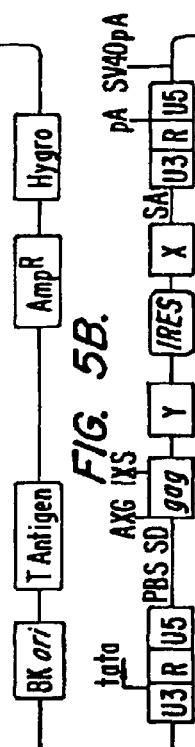
FIG. 5A.  FIG. 5B.  FIG. 5C.

VECTORS FOR DELIVERING VIRAL AND ONCOGENIC INHIBITORS

CROSS REFERENCE TO RELATED APPLICATIONS

This application is a continuation-in-part of U.S. Ser. No. 60/022,052, filed Jul. 22, 1997 by Ryback et al., which application is incorporated herein by reference in its entirety.

FIELD OF THE INVENTION

This invention relates to vectors for gene transfer and gene therapy, inhibition of viral and cancer cells by delivery of RNAses, recombinant cells and nucleic acids and the like.

BACKGROUND OF THE INVENTION

HIV-1 infection is epidemic world wide, causing a variety of immune system-failure related phenomena commonly termed acquired immune deficiency syndrome (AIDS). Recent studies of the dynamics of HIV replication in patients under antiviral therapy have reaffirmed the central role of the virus in disease progression, and provide a strong rationale for the development of effective, long term antiviral therapy (Coffin, J. M. *Science*, (1995) 267:483–489; Ho et al., *Nature* (1995) 373:123–6; Wei etal., *Nature* (1995) 373:117–22).

One interesting parameter from these studies is the extremely short life span of an HIV-1 infected CD4+ lymphocyte (half life=1–2 days), contrasting data from other studies which gave an estimated lifespan of months to years for uninfected lymphocytes (Bordignon et al., *Hum Gene Ther*. (1993) 4:513–20). These observations are relevant for intracellular immunization and antiviral gene therapy, because cells resistant to viral infection, or which suppress viral replication, are strongly selected for in vivo.

The molecular receptor for HIV is the surface glycoprotein CD4 found mainly on a subset of T cells, monocytes, macrophage and some brain cells. HIV has a lipid envelope with viral antigens that bind the CD4 receptor, causing fusion of the viral membrane and the target cell membrane, and release of the HIV capsid into the cytosol. HIV causes death of these immune cells, thereby disabling the immune system and eventually causing death of the patient due to complications associated with a disabled immune system. HIV infection also spreads directly from cell to cell, without an intermediate viral stage. During cell-cell transfer of HIV, a large amount of viral glycoprotein is expressed on the surface of an infected cell, which binds CD4 receptors on uninfected cells, causing cellular fusion. This typically produces an abnormal multinucleate syncytial cell in which HIV is replicated and normal cell functions are suppressed.

Pathogenicity of HIV-1 in vivo appears to be directly related to viral expression levels (for a review see Haynes, et al., *Science*, 271, 324–328 (1996)). Although drugs such as reverse transcriptase (RT) and protease inhibitors are effective over the short term, because of the emergence of resistance and side effects, their long term use remains problematic. For these reasons, several gene therapy approaches to prevent or interfere with viral replication at different stages of the HIV-1 life cycle are of interest. Antisense oligonucleotides, ribozymes, trans-dominant negative mutants of HIV-1 gene products, inducible suicide genes, intracellularly expressed antibodies against viral proteins, and molecular decoys for the Tat-inducible response region (TAR) and Rev responsive elements (RRE) have been used to inhibit HIV-1 replication (for an overview see, e.g., Yu, et al., *Gene Therapy*, 1, 13–26 (1994)).

More generally, anti-viral therapeutics, including anti-HIV therapeutics, can target, inter alia, viral RNAs (e.g., using ribozymes, or antisense RNA), viral proteins (RNA decoys, transdominant viral proteins, intracellular single chain antibodies, soluble CD4), infectible cells (suicide genes), or the immune system (in vivo immunization). Similar approaches can also be used for making therapeutics against cancer cells, e.g., by targeting oncogene products with ribozymes, transdominant proteins, and ligands such as antibodies which bind proteins encoded by the oncogene. However, all of these therapeutic approaches are hampered by the limitations of the delivery systems currently used to deliver anti-viral or anti-cancer therapeutics, and by the therapeutics themselves.

For instance, with regard to HIV treatment, the extensively used murine retroviral vectors transduce human peripheral blood lymphocytes poorly, and fail to transduce non-dividing cells such as monocytes/macrophages, which are known to be reservoirs or mediators of many viral infections and cancerous conditions. An appealing alternative basis for therapeutic vectors would be to utilize HIV-based delivery systems, which would ensure optimal CD4+ cell targeting and intracellular co-localization of HIV target and gene therapeutic effector molecules. In addition, HIV-derived vectors could be packaged by wild type HIV virions of HIV-infected patients in vivo, and thereby be replicated and disseminated to a larger pool of potentially HIV-infectible cells upon infection by HIV. Some of the regulatory elements which could be used in such vectors (e.g. TAR, RRE and packaging signal sequences) would themselves be antagonistic to HIV replication (i.e., they would act as molecular decoys), thereby providing an additional level of HIV inhibition.

The capacity to infect quiescent cells, which is not shared by oncoretroviruses or MoMLV-derived retroviral vectors, also provides the possibility of using HIV-based vectors to target therapeutics for treatment of other viral conditions and of various cancers. HIV-based vectors which stably transfer genes to rarely dividing stem cells and post-mitotic cells in the hematopoietic, nervous, and other body systems are desirable. Such vectors could be used to treat HIV infections, and many other disorders which are mediated by target cells infectable by HIV, or transducible by HIV-based vectors.

HIV cell transformation vectors can be used to transduce non-dividing hematopoietic stem cells (CD34+), e.g., by pseudotyping the vector. These stem cells differentiate into a variety of immune cells, including CD4+cells which are the primary targets for HIV infection. CD34+ cells are a good target for ex vivo gene therapy, because the cells differentiate into many different cell types, and because the cells are capable of re-engraftment into a patient undergoing ex vivo therapy. The vesicular stomatitis virus envelope glycoprotein (VSV-G) has been used to construct VSV-G-pseudotyped HIV vectors which can infect hematopoietic stem cells (Naldini et al. (1996) *Science* 272:263 and Aldina et al. (1996) *J. Virol* 70:2581).

Existing vectors and therapeutics have several features which could be improved. One is the narrow specificity of the antiviral molecules, which can have a limited beneficial effect when considered in light of the genetic plasticity of HIV-1. Resistant variants may arise, similar to the situation with more common anti-viral drugs. A second problem is loss of expression of anti-viral genes, which can occur against antiviral proteins because of immune responses against foreign therapeutic proteins. Loss of expression can also occur with polymeric TAR and RRE molecules by deletion through recombination. A third problem is that expression of protective gene is optionally regulated to occur only when needed, i.e., in infected cells, in order to minimize unintended side effects.

Accordingly, there is a need for improved HIV-based vectors for delivering existing anti-viral genes to cells in vitro, ex vivo and in vivo, and for improved therapeutics against viruses which infect cells transduced by HIV-based vectors (including HIV), and against cancer and other disorders which occur in, or are mediated by, cells which can be transduced by HIV-based vectors. This invention fulfills these and other needs.

SUMMARY OF THE INVENTION

The present invention provides cell transduction vectors for inhibiting viral replication in cells transduced with the vectors. The vectors also inhibit the growth of cancerous cells.

In one class of embodiments, the cell transduction vector comprise a vector nucleic acid encoding a first viral inhibitor subsequence. The subsequence encodes a nucleic acid or protein which interferes with the life cycle of a virus in a cell transduced by the vector. Inhibitors include RNA decoys, transdominant viral proteins, soluble cell receptors which serve as the means of entry for the particular virus (e.g., CD4), suicide genes, antisense oligonucleotides, ribozymes, transdominant negative mutants of viral gene products (transdominant Δgag, transdominant forms of Rev and Tat, and the like), inducible suicide genes, intracellularly expressed antibodies against viral proteins and molecular decoys for viral transcription factors (e.g., Tat or Rev). In one particularly preferred class of embodiments, RNAse enzymes, such as those in the RNAse A superfamily, are used as viral inhibitors. For example, as described herein, it is now surprisingly discovered that human eosinophil-derived neurotoxin (EDN) is an effective inhibitor of HIV. Other preferred RNAses include Onconase and Onconase-derived RNAses.

Oncogene inhibitors are optionally incorporated into the vectors of the. invention. Many of the viral inhibitors described above are also oncogene inhibitors. For example, RNAse enzymes from the RNAse a superfamily (including EDN, Onconase and Onconase-derived RNAses) are oncogene inhibitors. Other preferred oncogene inhibitors include antibodies against oncogene products such as Ras.

The viral and oncogene inhibitors of the invention are typically operably linked to a promoter. The promoter can be a constitutive promoter, an inducible promoter or a tissue-specific promoter. Preferred promoters include retroviral LTR promoters, particularly those derived from HIV, the CMV promoter, the probasin promoter and tetracycline-responsive promoters.

In one embodiment, the vector nucleic acids of the invention comprise a splice donor site subsequence and a splice acceptor site subsequence. Typically, the first viral inhibitor is located between the splice donor and splice acceptor site. Optionally, the second viral inhibitor is located between the splice donor and splice acceptor site. Splicing of the transcript in the nucleus optionally inhibits translocation of nucleic acid encoding the viral inhibitor into the cytosol, thereby inhibiting translation of the viral inhibitor. In a preferred embodiment, the vector comprises a Rev binding site such as a retroviral RRE. In the presence of Rev (which occurs, e.g., upon infection of the cell with a retrovirus such as HIV), splicing of the vector nucleic acid is inhibited, facilitating production of viral inhibitors encoded by the vector. Rev also facilitates transport of nucleic acids encoded by the vector, such as mRNAs encoding viral inhibitors into the cytosol.

The cell transduction vectors of the invention optionally comprise targeting components which facilitate introduction of vector nucleic acids into target cells. The targeting moieties optionally include retroviral particles, pseuduotyped retroviral particles (e.g., HIV-based retroviral particles comprising VSV-G envelope proteins), and cell receptor ligands (e.g., transferrin, c-kit, and viral receptor ligands, cytokine receptors, interleukin receptors and the like) complexed to the vector nucleic acid (e.g., using poly-L-lysine or other polycations).

Preferred vector nucleic acids of the invention encode multi-cistronic RNAs, wherein each of the open reading frames in the multi-cistronic RNA optionally encode one or more viral and/or oncogene inhibitors. The cistrons optionally encode nucleic acids and proteins other than inhibitors, e.g., reporting molecules such as a green fluorescent protein, or a luciferase. Translation of cistrons with internal translation start sequences are initiated at internal ribosome entry sites such as the encephalomyocarditis virus internal ribosome entry site (IRES).

In preferred embodiments, the vector nucleic acids of the invention comprise a retroviral packaging site. This packaging site directs packaging of the vector nucleic acid into retroviral capsids. For example, vectors comprising the psi site of HIV are packaged into HIV particles. This provides two advantages to the vector. First, vector nucleic acids packaged into retroviral particles can be delivered to cells within the host range of the retrovirus. For example, vector nucleic acids packaged into HIV particles can be transduced into CD4+ cells. Second, HIV particles can be pseudotyped with VSV-G envelope protein to permit transduction of the vector nucleic acid into CD34+ hematopoietic stem cells. The infective range of retroviral particles can also be extended using amphotropic retroviruses, or by complexing cell targeting agents such as antibodies, cell receptors and the like with the retroviral particle.

The cell transduction vectors of the invention optionally include retroviral chromosome integration subseqences which facilitate integration of vector nucleic acid into the chromosome of a host cell. For example, nucleic acid subsequences of interest in the vector nucleic acids are typically placed between retroviral LTRs, which facilitate integration of nucleic acid subsequences located between the retroviral LTRs into the host chromosome. Example LTRs are those from an HIV (e.g., HIV-1 or HIV-2) virus or viral clone.

In some embodiments, the cell transduction vector of the invention comprises a liposome to facilitate delivery of the vector nucleic acid to a target cell. In addition to, or in place of the liposome, the vectors optionally include cell targeting ligands, polycationic moieties for complexing vector nucleic acids to cell targeting ligands, and the like.

In other embodiments, the vectors of the invention are optionally placed into a composition comprising a pharmaceutical excipient, e.g., for injection into a mammal.

Three example vectors of the invention are pBAR, pBAR-ONC and pBAR-EDN. Conservative modifications of the vectors are made using routine recombinant techniques.

Cells comprising the cell transduction vectors of the invention are also a feature of the invention. Example cells include CD4+ cells, CD34+ hematopoietic stem cells, and cells comprising the transferrin receptor.

Methods of transducing cells are also provided. In the methods of the invention, a cell is contacted with a vector of the invention. The vector nucleic acid is transduced into the cell, thereby providing a way of expressing nucleic acids and proteins encoded by the vector. The method is used to transduce cells in vitro, ex vivo, and in vivo. The cells can be present in cell culture, isolated from a mammal, or present in a mammal. The cells are optionally isolated from a mammal and subsequently re-introduced into the mammal.

In one preferred class of embodiments, the vectors of the invention are used to transduce cells of the invention with viral inhibitors, thereby inhibiting the infection, replication or spread of the virus in the cell, or through a population of cells (e.g., a cell culture, cell isolate, or a mammal). For example, the vectors and methods of the invention can be used to inhibit HIV. Preferred cells for transduction include CD4+ and CD34+ cells, in vitro, ex vivo or in vivo.

In one embodiment, the transformed cells are hematopoietic stem cells such as CD34+ stem cells. Stem cells transformed by the methods are typically introduced into a mammal. In one particular embodiment, the cell transformation vector encodes an anti-HIV agent such as a ribonuclease which cleaves an HIV nucleic acid. In this embodiment, cells transformed with the vectors and their differentiated progeny are HIV-resistant.

DESCRIPTION OF THE DRAWING

FIG. 4 shows sequence details of pBAR-EDN (SEQ ID NOS: 1–3).

FIG. 5 shows 6 variants of pBAR.

DEFINITIONS

Figure 1:
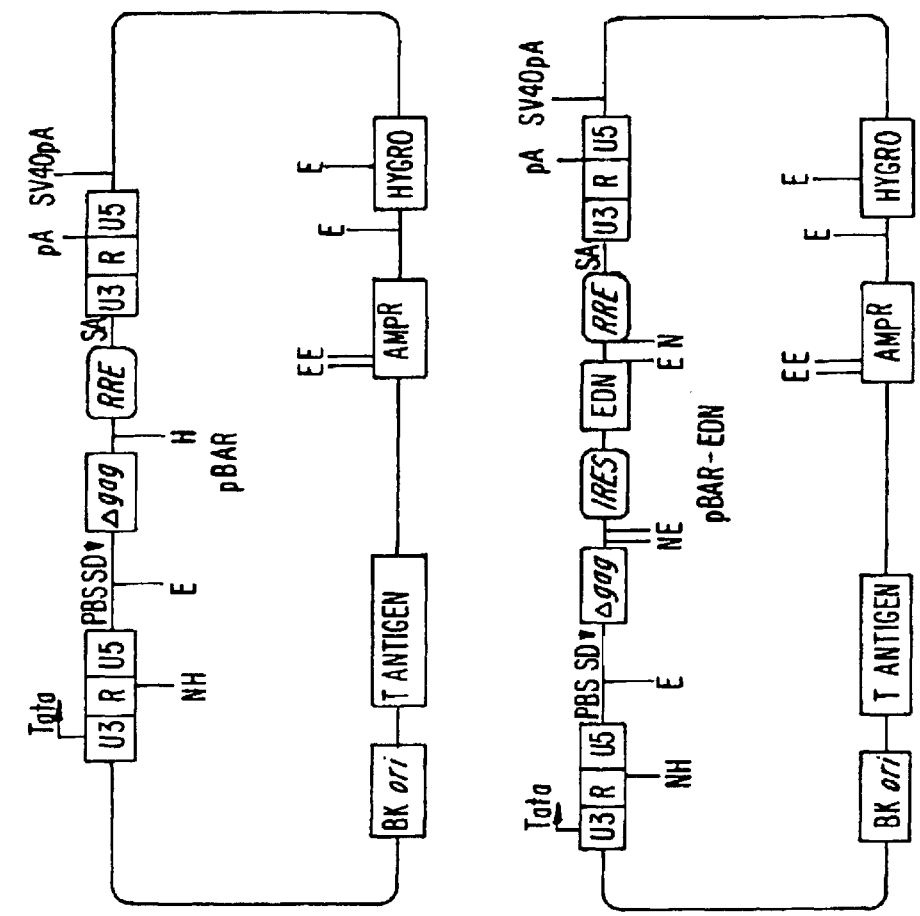
FIG. 1 shows features of HIV-1 inducible vectors.
Figure 2A:
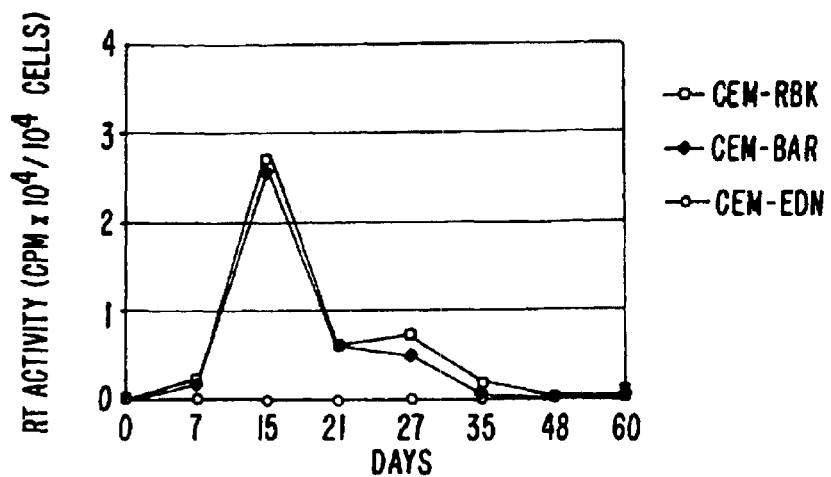
FIG. 2 shows the RT activity and p24 production in the supernatant of transduced CEM after HIV-1 infection. Cells were infected with different estimated MOI (2, 0.2, 0.02) of HIV-$1_{MB}$ and cell culture supernatants were assayed for RT activity and p24 production on the days indicated by the open square (CEM-RBK), the diamond (CEM-BAR) or the filled circle (CEM-EDN).
Figure 2B:
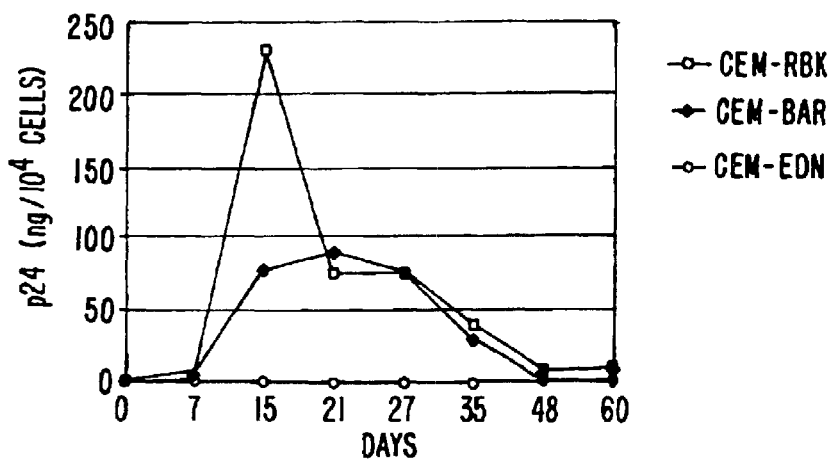
Figure 2C:
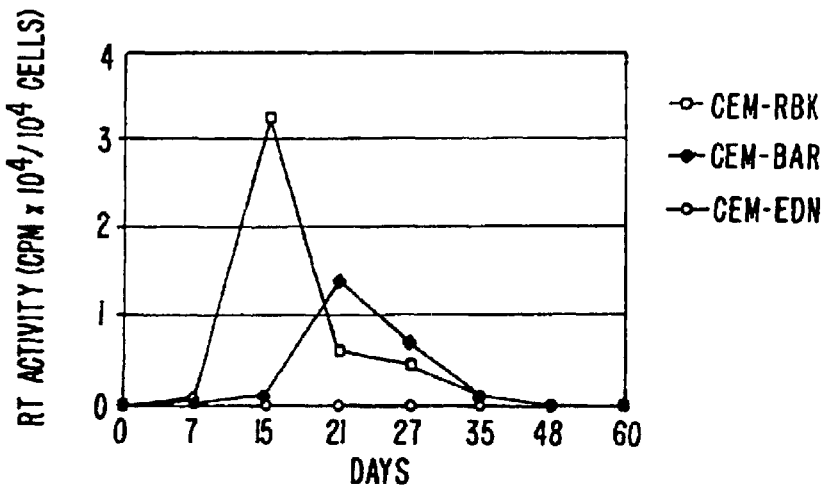
Figure 2D:
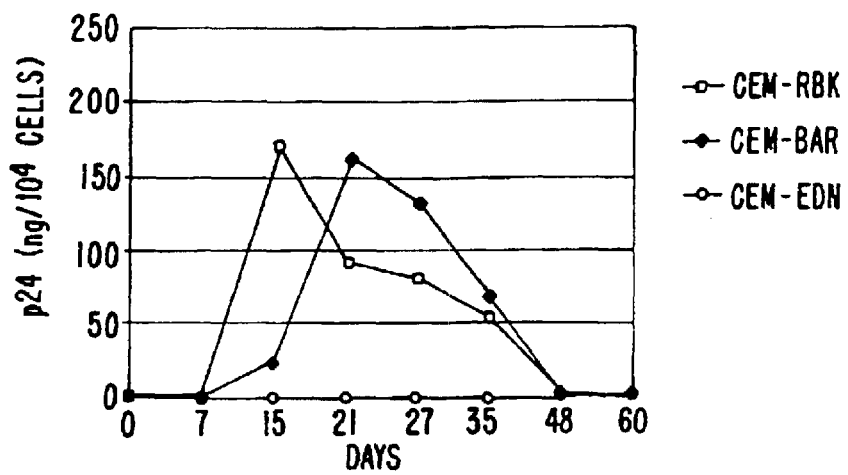
Figure 2E:
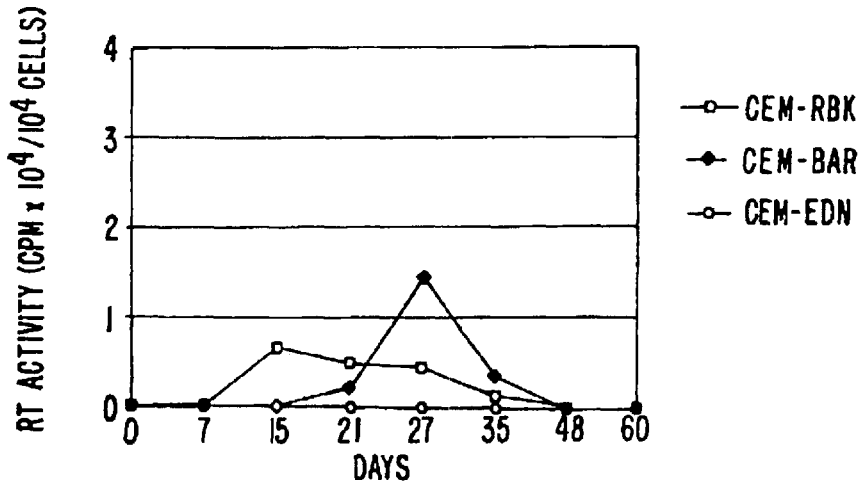
Figure 2F:
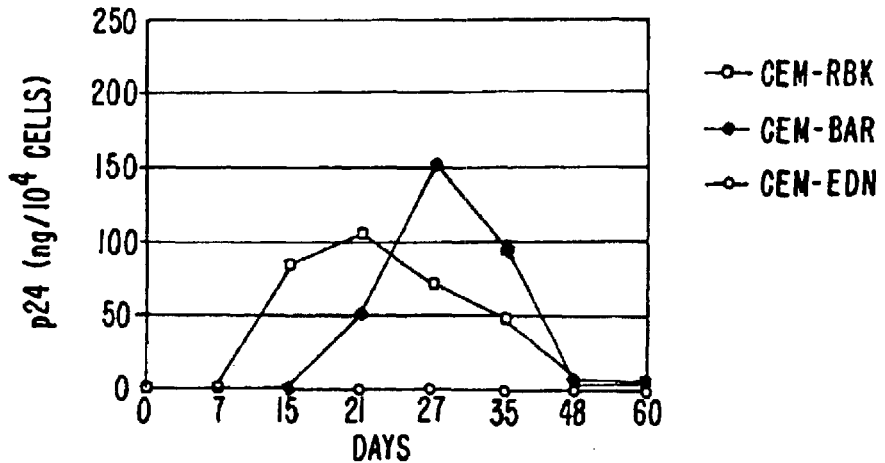
Figure 3:
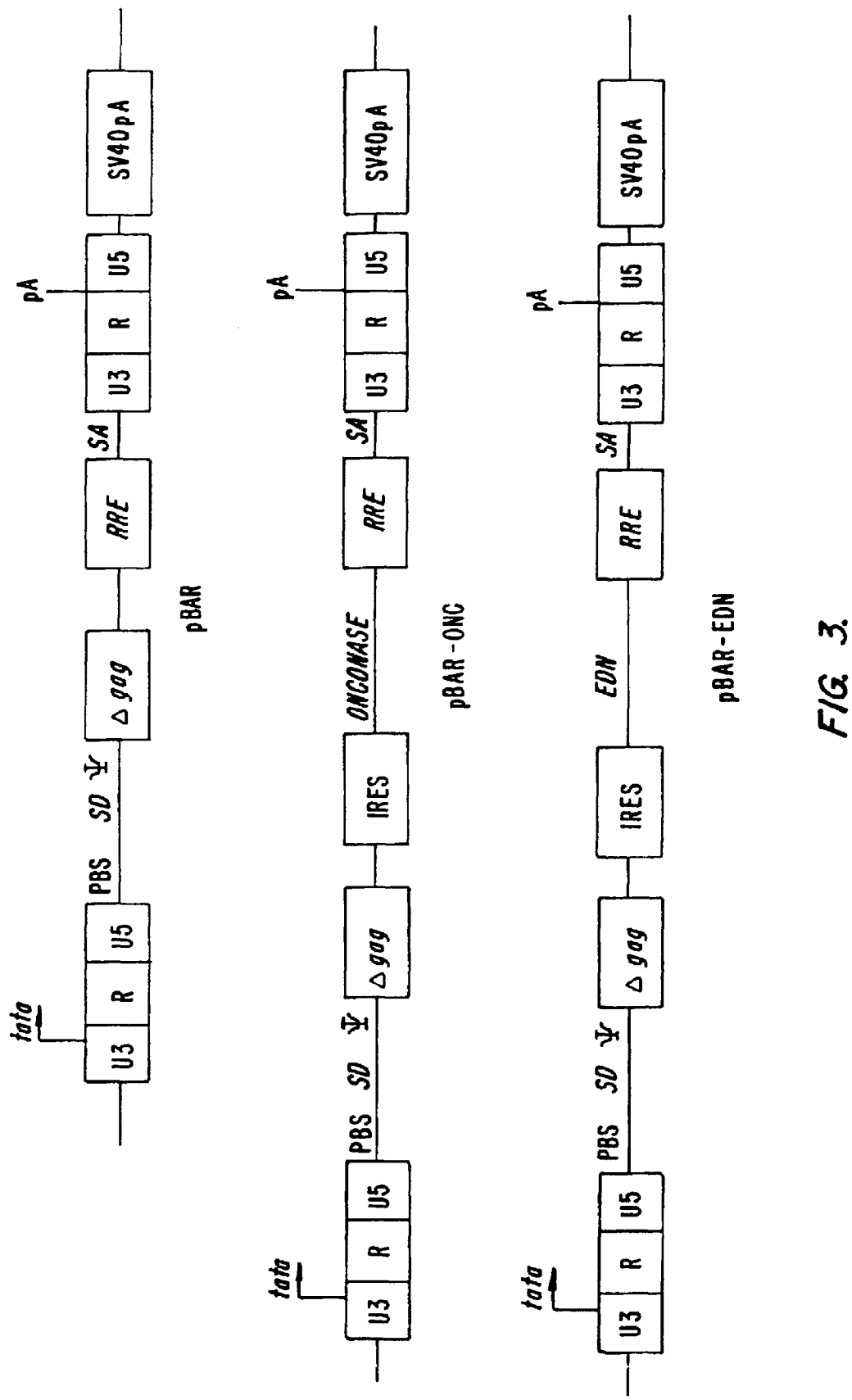
FIG. 3 shows an alignment between pBAR, pBAR-ONC, and pBAR-EDN.
Figure 6A:
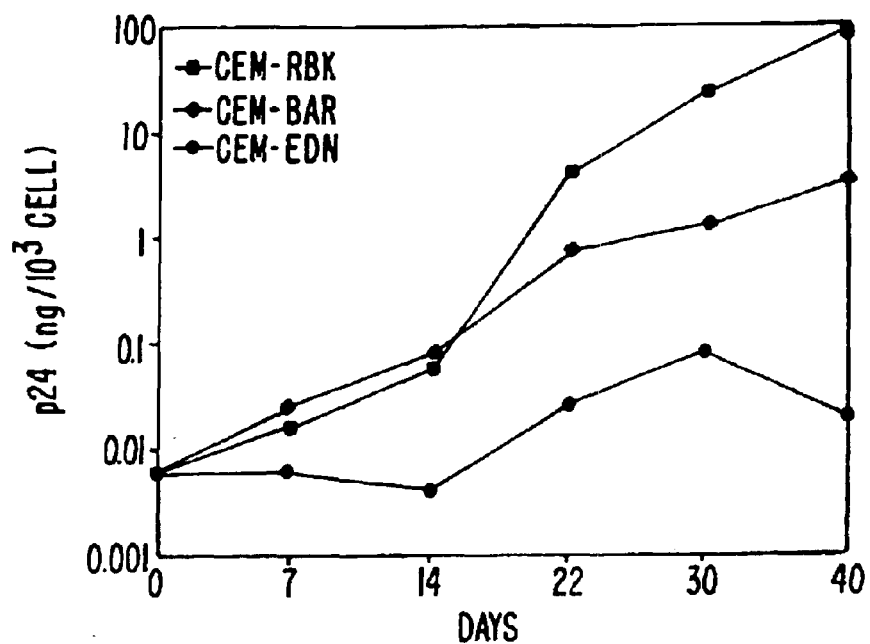
FIG. 6, panels A and B provide graphs of a time course analysis of p24 recovery following infection with primary HIV field isolates
Figure 6B:
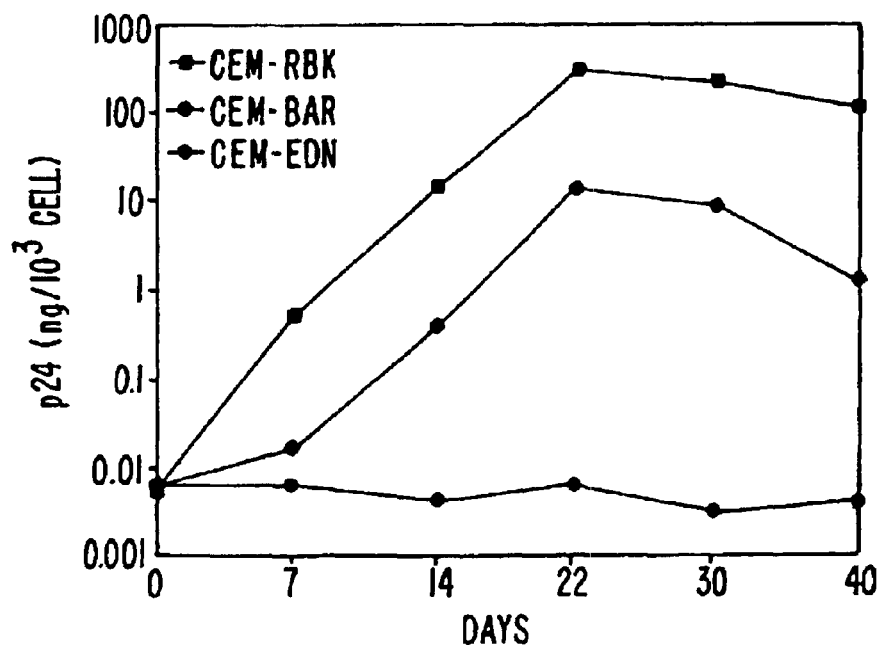
Figure 7:
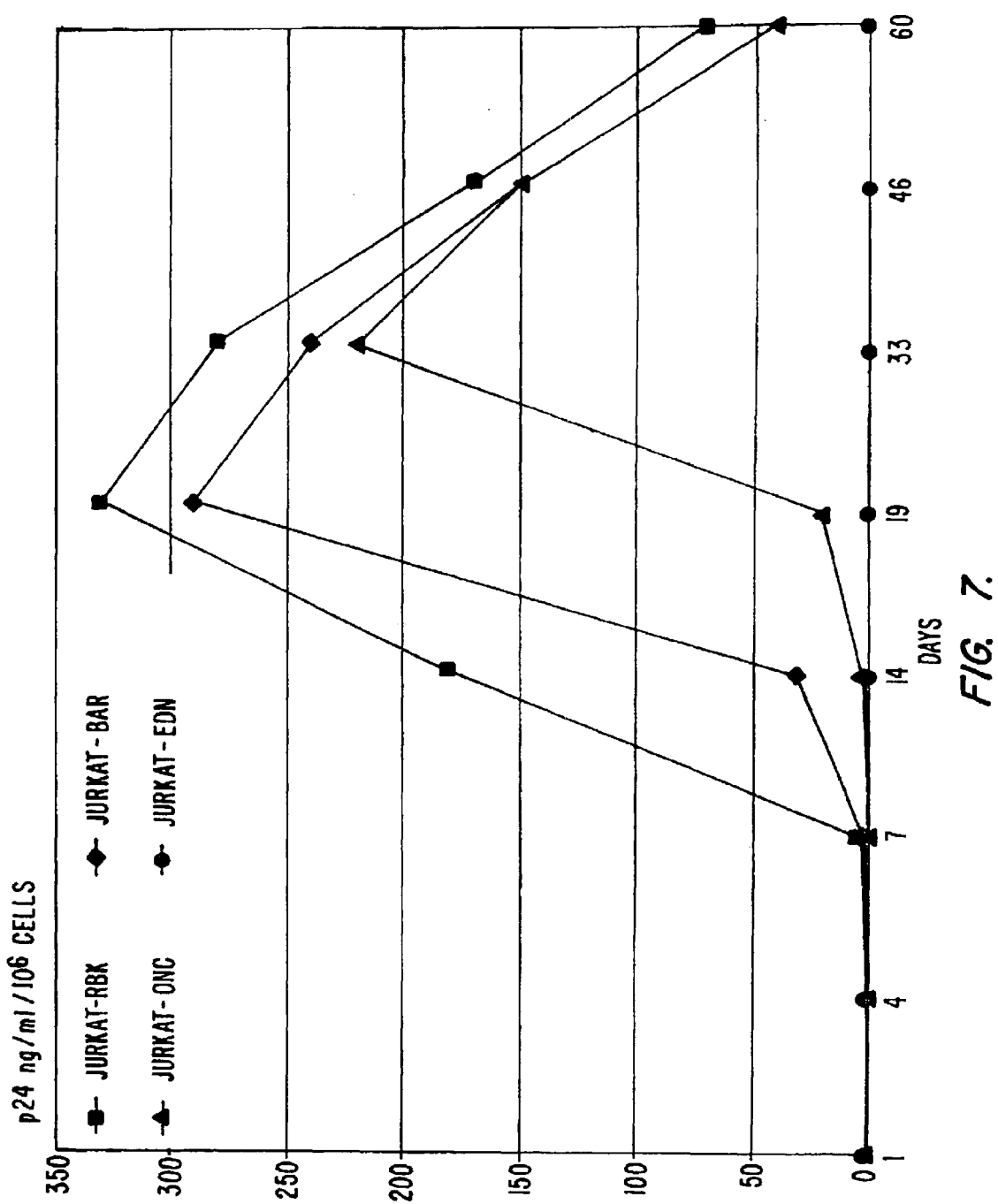
FIG. 7 is a graph of a time course of p24 production in Jurkat cells.

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York); Walker (ed) (1988) *The Cambridge Dictionary of Science and Technology*, The press syndicate of the University of Cambridge, N.Y.; and Hale and Marham (1991) The Harper Collins Dictionary of Biology Harper Perennial, NY provide one of skill with a general dictionary of many of the terms used in reference to this invention. Paul (1993) Fundamental Immunology, Third Edition Raven Press, New York, N.Y. and the references cited therein provide one of skill with a general overview of the ordinary meaning of many of the virally or immunologically related terms herein. Although any methods and materials similar or equivalent to those described herein can be used in the practice or testing of the present invention, certain preferred methods and materials are described in detail. For purposes of the present invention, the following terms are defined below.

A "vector" is a composition which can transduce, transfect, transform or infect a cell, thereby causing the cell to replicate or express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell, nor that any particular cell type is the subject of transduction. A cell is "transformed" by a nucleic acid when the nucleic acid is transduced into the cell and stably replicated. A vector includes a nucleic acid (ordinarily RNA or DNA) to be expressed by the cell. This nucleic acid is referred to as a "vector nucleic acid." A vector optionally includes materials to aid in achieving entry of the nucleic acid into the cell, such as a viral particle, liposome, protein coating or the like. A "cell transduction vector" is a vector which encodes a nucleic acid which is expressed in a cell once the nucleic acid is transduced into the cell.

The HIV "Tat" protein encoded by tat binds to the TAR stem loop structure, facilitating synthesis of RNA from the HIV genome. The HIV "Rev" protein is a nuclear phosphoprotein which binds to the RRE to mediate export of structural mRNA from the nucleus to the cytoplasm. The HIV "Gag" proteins are encoded by the HIV gag gene and form the core and matrix of the HIV virion and affect the processes of budding and viral assembly. Several virion proteins are encoded by gag, including p24, p9, p7, p55 and p16. The genes of the HIV genome, including gag, rev and tat are well known. See, e.g., Dalgleish and Weiss in Principles and Practice of Clinical Virology 3rd edition (Zuckerman et al. eds) John Wiley & Sons, Chichester England and the references therein; Haseltine and Wong-Staal (eds) *Harvard Institute Series on Gene Regulation of Human Retroviruses Volume 1: Genetic Structure and Regulation of HIV* Raven Press New York; and Paul, supra. A variety of HIV clones have been fully sequenced. See, e.g., Ratner et al. (1987) *AIDS Research and Human Retroviruses* 3(1): 57–69.

Transdominant forms of Gag, Rev and Tat (Δ-gag, Δ-Rev and Δ-Tat) are known. Transdominant proteins typically interact with or compete with the naturally occurring form of the corresponding protein, thereby inhibiting the function of the naturally occurring form of the protein. For example, tat and rev can be mutated so that the encoded proteins retain the ability to bind to TAR and RRE, respectively, but to lack the proper regulatory function of those proteins. See, e.g., Nabel et al. (1994) *Human Gene Therapy* 5:79–92. A comparison of the effects of trans dominant Tat and Rev is found in Bahner et al. (1993) *Journal of Virology* 67(6): 3199. Delta-gag has been shown to inhibit HIV-1 replication, presumably by interfering with viral assembly (Trono, et aL, *Cell*, 59, 113–120 (1989); Lori, et al., *Gene Therapy*, 1, 27–31 (1994)).

A "splice donor site" refers to a 5' splice junction site which substantially matches a 5' consensus sequence, wherein the site is at an intron-exon boundary in a pre-mRNA found, e.g., in the nucleus of a cell. See, Watson et al. (1987) *Molecular Biology of the Gene, Fourth Edition* The Benjamin/Cummings Publishing Co., Menlo Park, Calif. for an introduction to gene splicing. In RNA molecules which comprise a Rev binding site, splicing is typically inhibited in the presence of Rev. A "splice acceptor" site refers to a 3' splice junction site which substantially matches a 3' splice consensus sequence, wherein the site is at an intron-exon boundary in a pre-mRNA found, e.g., in the nucleus of a cell. In RNA molecules which comprise a Rev binding site, splicing is typically inhibited in the presence of Rev. A "Rev binding site" is a nucleic acid subsequence to which Rev binds. A "retroviral Rev binding subsequence" is a Rev binding site derived from a retrovirus. Several such sequences are known, including the Rev RRE, RRE subsequences, and cognate sequences from a variety of retroviruses.

A "viral inhibitor" or "anti-viral agent" refers to any nucleic acid or molecule encoded by nucleic acid which inhibits the replication of a virus in a cell, or which upon translation or transcription inhibits replication of a virus in a cell. In addition, nucleic acids which substantially encode a molecule which inhibits replication of a virus in a cell, but which are not expressible or translatable are considered inhibitors for purposes of this disclosure. For example, a nucleic acid substantially encoding a transdominant Gag protein is considered an inhibitor, even if the nucleic acid lacks a start codon. "Viral inhibition" refers to the ability of a construct to inhibit the infection, growth, integration, or replication of a virus in a cell. Inhibition is typically measured by monitoring changes in a cell's viral load (i.e., the number of viruses and/or viral proteins or nucleic acids present in the cell, cell culture, or organism) or by monitoring resistance by a cell, cell culture, or organism to viral infection. An "oncogene inhibitor" is an agent which inhibits the replication, growth or metastasis of a tumor cell when expressed in the cell. The tumor cell is optionally in cell culture, or a primary isolate from a mammal, or is an in vivo cell, e.g., present in a tumor in a mammal. One class of preferred inhibitors inhibits the replication, growth or metastasis of prostate tumor cells.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "recombinant nucleic acid" comprises or is encoded by one or more nucleic acids that are derived from a nucleic acid which was artificially constructed. For example, the nucleic acid can comprise or be encoded by a cloned nucleic acid formed by joining heterologous nucleic acids as taught, e.g., in Berger and Kimmel, *Guide to Molecular Cloning Techniques, Methods in Enzymology* volume 152 Academic Press, Inc., San Diego, Calif. (Berger) and in Sambrook et al. (1989) *Molecular Cloning—A Laboratory Manual* (2nd ed.) Vol. 1–3 (Sambrook). Alternatively, the nucleic acid can be synthesized chemically. The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell or a progenitor of the cell by artificial means.

The terms "isolated" or "biologically pure" refer to material which is substantially or essentially free from components which normally accompany it as found in its native state. "Encapsidation" generically refers to the process of incorporating a nucleic acid sequence (e.g., a provirus) into a viral particle. In the context of HIV, the nucleic acid is typically an RNA. A "viral particle" is a generic term which includes a viral "shell", "particle" or "coat", including a protein "capsid", a "lipid enveloped structure", a "protein-nucleic acid capsid", or a combination thereof (e.g., a lipid-protein envelope surrounding a protein-nucleic acid particle, as occurs in retroviruses).

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "subsequence" in the context of a particular nucleic acid sequence refers to a region of the nucleic acid equal to or smaller than the specified nucleic acid. Thus, for example, a viral inhibitor nucleic acid subsequence is a subsequence of a vector nucleic acid, because, in addition to encoding the viral inhibitor, the vector nucleic acid optionally encodes other components such as a promoter, a packaging site, chromosome integration sequences and the Like.

Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An overview to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y.

"Stringent conditions" in the context of nucleic acid hybridization are sequence dependent and are different under different environmental parameters. An extensive guide to the hybridization of nucleic acids is found in Tijssen (1993), id. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11–17 (1988); Smith and Waterman (1981) *Adv. Appl. Math.* 2: 482; Needleman and Wunsch (1970) *J. Mol. Biol.* 48: 443; Pearson and Lipman (1988) *Proc. Natl. Acad. Sci. USA* 85: 2444; Higgins and Sharp (1988) *Gene*, 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1 %) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (X);
5) Isoleucine (1), Leucine (L), Methionine. (M), Valine (V); and
6) Phenylalanine (F), Tyrosine (Y), Tryptophan (W).

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_l$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce P(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

DETAILED DESCRIPTION OF THE INVENTION

Vectors for gene delivery are provided. The vectors comprise vector nucleic acids with viral or oncogene inhibitors such as ribonucleases. For example, it is surprisingly discovered that the ribonuclease EDN (eosinophil-derived neurotoxin) has potent anti-HIV activity when expressed in a cell. Prior art studies regarding the effect of EDN on HIV concluded that EDN had no such HIV inhibitory effect (See, Youle et al. (1994) *Proc. Natl. Acad. Sci. USA*). Other preferred inhibitors include other members of the RNAse A superfamily, which have both anti-tumor and anti-viral activity.

These inhibitors are placed under the control of a promoter which optimizes expression of the inhibitor with regard to the virus or oncogene to be inhibited. For example, the inhibitors are preferably placed under the control of a retroviral LTR promoter when the inhibitors are used to inhibit retroviral expression in a cell. For example, the HIV LTRs are optionally used to direct inhibitor expression in a cell. The LTR is up-regulated in the presence of HIV, thereby inhibiting HIV replication in the cell upon infection of the cell by HIV.

A second level of control is optionally provided by placing the viral inhibitor between splice sites, and providing a Rev binding site to inhibit splicing in the presence of Rev. In the absence of Rev, inhibitor nucleic acids are spliced out of the pre-mRNA, and are not translated. In the presence of Rev (e.g., upon infection by a retrovirus encoding Rev), the inhibitor nucleic acid is not spliced, and is translated to produce an active inhibitor.

A third level of control is optionally provided by encoding two or more separate inhibitors in a multicistronic message under the control of the selected promoter. This avoids the possibility of promoter interference preventing transcription of one nucleic acid due to expression of a second proximal transcription unit. To permit translation of the various viral inhibitors encoded by the muiti-cistronic message, internal ribosome entry sites are provided upstream of internal open reading frames in the polycistronic message.

In many embodiments, the vectors include sequences for packaging and chromosomal integration, thereby providing a secondary protective effect upon infection by an infective virus due to packaging and dissemination of the vector by the infective virus.

One example construct, pBAR, contains a trans-dominant negative gag mutant, delta-gag, which has been shown to inhibit HIV-1 replication, by interfering with viral assembly (Trono, et al., *Cell*, 59, 113–120 (1989); Lori, et al., *Gene Therapy*, 1, 27–31 (1994)). Another construct contains both delta-gag and a gene encoding eosinophil derived neurotoxin factor (EDN), a member of the ribonuclease A superfamily, which is relatively unselective from the standpoint of the structure of the RNA (Newton, et aL, *J. Biol. Chem.*, 269, 26739–26745 (1994)). The protective genes are expressed from a dicistronic MRNA and the translation of both coding sequences is ensured by an internal ribosome binding site (IRES) between the two coding regions. The construct uses the HIV-1 LTR as a promoter and contains splice donor and acceptor sites; consequently, expression is regulated both by Tat, at the level of the RNA synthesis, and Rev at the level of RNA splicing and transport.

Finally, the construct contains a functional HIV-1 packaging signal, potentially allowing its spread by pseudotyping to a variety of cell types, and providing a secondary protective effect upon infection by HIV. These constructs inhibit HIV-1 replication.

Cloning, Nucleic Acids and Proteins

Given the strategy for making the vector nucleic acids of the present invention, one of skill can construct a variety of clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of ski through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a Joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acids sequenced by this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

In vitro amplification techniques suitable for amplifying sequences to provide a large nucleic acid or for subsequent analysis, sequencing or subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et aL eds) Academic Press Inc. San Diego, Calif. (1990) (Innjis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science*, 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426, 039. Improved methods of amplifying large nucleic acids are summarized in Cheng et al. (1994) *Nature* 369: 684–685 and the references therein. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

Oligonucleotides for e.g., in vitro amplification methods, or for use as gene probes are typically chemically synthesized according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

The polypeptides of the invention can be synthetically prepared in a wide) variety of well-know ways. For instance, polypeptides of relatively short length can be synthesized in solution or on a solid support in accordance with conventional techniques. See, e.g., Merrifield (1963) *J. Am. Chem. Soc.* 85:2149–2154. Various automatic synthesizers are commercially available and can be used in accordance with known protocols. See, e.g., Stewart and Young (1984) *Solid Phase Peptide Synhesis*, 2d. ed., Pierce Chemical Co.

Making Conservative Modifications of the Nucleic Acids and Polypeptides of the Invention.

One of skill will appreciate that many conservative variations of the inhibitors and vectors disclosed yield essentially identical inhibitors and vectors. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted variations of each explicitly disclosed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8;81–97; Roberts et al. (1987) *Nature* 328:731–734 and Sambrook, Innis, Ausbel, Berger, Needham VanDevanter and Mullis (all supra).

Most commonly, amino acid sequences are altered by altering the corresponding nucleic acid sequence and expressing the polypeptide. However, polypeptide sequences are also optionally generated synthetically on commercially available peptide synthesizers to produce any desired polypeptide (see, Merrifield, and Stewart and Young, supra).

With regards to HIV inhibitors and vectors, one can select a desired nucleic acid or polypeptide of the invention based upon the sequences and constructs provided and upon knowledge in the art regarding HIV strains generally. The life-cycle, genomic organization, developmental regulation and associated molecular biology of HIV strains have been the focus of well over a decade of intense research. Similarly, the molecular basis of cancer has been studied intensely since the advent of molecular biology. The specific effects of many inhibitors are known, and no attempt is made herein to catalogue all such known interactions.

Moreover, general knowledge regarding the nature of proteins and nucleic acids allows one of skill to select appropriate sequences with activity similar or equivalent to the nucleic acids, vectors and polypeptides disclosed herein. The definitions section herein describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Packaging Vectors in Retroviral Particles

In one embodiment, the vectors of the invention are derived from retroviral clones (e.g., HIV), and or/are packaged by retroviral clones. Many such clones are known to persons of skill, and publicly available. Well-established repositories of sequence information include GenBank, EMBL, DDBJ and the NCBI. Furthermore, viral clones can be isolated from wild-type retroviruses using known techniques. For example, where the retrovirus is HIV, a lambda-phage clone containing a full-length provirus is obtained from the genomic DNA of a lymphoblastic cell line infected with an HIV strain isolated from the peripheral blood mononuclear cells of an HIV seropositive AIDS patient. The virus is replication competent in vitro, producing p24 protein and infectious progeny virions after direct transfection into CD4+ cells. Appropriate cells for testing infectivity include well characterized established human T-cells such as Molt-4/8 cells, SupT1 cells, H9 cells, C8166 cells and myelomonocytic (U937) cells as well as primary human lymphocytes, and primary human monocyte-macrophage cultures.

In general, a complete virulent viral genome can be used to make a packaging vector. For example, "a full-length HIV genome" in relation to an HIV-1 packaging vector consists of a nucleic acid (RNA or DNA) encoded by an HIV virus or viral clone which includes the 5' and 3' LTR regions and the genes between the LTR regions which are present in a typical wild-type HIV-1 virus (e.g., env, nef, rev, vpx, tat, gag, pol, vif, and vpr).

Packaging vectors are made by deleting the packaging site from a full-length genome. Specific mutations in the HIV packaging site are described, e.g., in Aldovini and Young (1990) *Journal of Virology* 64(5):1920–1926. The RNA secondary structure of the packaging site is described in Clever et al. (1995) *Journal of Virology* 69(4): 2101–2109. The stem loops of the psi site for HIV-1 are described in Clever.

A substantial deletion in the region between the major splice donor site ("MSD") and the beginning of the gag gene is usually performed to disable a packaging viral genome.

The resulting deletion clones can be used to make viral particles, by transducing the deletion clone into a packaging cell (typically a Hela cell) and expressing the clone. Because the clones lack the HIV packaging site, they are not packaged into viral particles which they encode. However, cells transduced with the packaging clone produce all of the factors necessary for packaging HIV packageable nucleic acids (i.e., nucleic acids comprising an HIV packaging site). The packaging clone is either co-transfected into the packaging cell with a packageable vector nucleic acid of the invention, or is stably expressed by the packaging cell. When the vector nucleic acid comprises an appropriate packaging site, it is packaged by the trans products of the packaging vector.

Packageable vector nucleic acids encode an RNA which is competent to be packaged by a retroviral particle. Such nucleic acids can be constructed by recombinantly combining a packaging site with a nucleic acid of choice. The packaging site (psi site) is located adjacent to the 5' LTR, primarily between the MSD site and the gag initiator codon (AUG) in the leader sequence of the gag gene for HIV. Thus, the minimal HIV-1 packaging site includes a majority of nucleic acids between the MSD and the gag initiator codon from either HIV-1 or HIV-2. See also, Clever et al., supra and GarzinoDemo et al. (1995) *Hum. Gene Ther.* 6(2): 177–184. For a general description of the structural elements of the HIV genome, see, Holmes et al. PCT/EP92/02787. Preferably, a complete packaging site includes sequences from the 5' LTR and the 5' region of gag gene for maximal packaging efficiency. These packaging sequences typically extend about 100 bases into the coding region of gag or further, and about 100 bases into the HIV 5' LTR or further. Often as much as 500–700 nucleotides of gag are included.

Viral and Oncogene Inhibitors

Certain viral and oncogene inhibitors are known in the art. The literature describes such genes and their use. See, for example, Yu et al. (1994) *Gene Therapy*, 1:13; Herskowitz (1987) *Nature*, 329:212 and Baltimore (1988) *Nature*, 335:395. Viral inhibitors useful in this invention include, without limitation, ribonucleases, anti-sense genes, ribozymes, decoy genes, transdominant genes/proteins and suicide genes.

(i) Ribonucleases

Preferred inhibitors of the invention include ribonucleases such as those from the RNAse A superfamily. Ribonucleases from the RNAse A superfamily include those described in copending U.S. Provisional Patent Application U.S. Ser. No. 60/011,800 filed Feb. 21, 1996 by Rybak et al. (incorporated herein by reference). See also, Bond et al. (1989) *Biochemistry* 28: 8262; Beintema er al. (1988) *Prog. Biophys. Mol. Biol.* 51: 165; Rosenberg et al. (1989) *J. Exp. Med* 170: 163, and Rosenberg et al. (1989) *Proc. Natl. Acad. Sci. USA* 86: 4460. Many such members are known and include, but are not limited to, frog lectin from Rana catesbaiana (Titani et al., *Biochemistry* 26:2189 (1987)); ONCONASE (Rosenberg et al., *Proc. Natl. Acad. Sci. USA* 86:4460 (1989)); eosinophil derived neurotoxin (EDN) (Rosenberg et al., supra); human eosinophil cationic protein (ECP) (Rosenberg et al., *J. Exp. Med*. 170:163 (1989)); angiogenin (ANG) (Fodstad et al., *Cancer Res*. 44:862 (1984)); bovine seminal RNase (Preuss et al., *Nuc. Acids. Res.* 18:1057 (1990)); and bovine pancreatic RNase (Beintama et al., *Prog. Biophys. Mol. Biol.* 51:165 (1988)). Amino acid sequence alignment for such RNases are also set out in Youle et al., *Crit. Rev. Ther. Drug. Carrier Systems* 10:1–28 (1993)

Telomerase is a "universal cancer target" (G. B. Morin, *JNCI*. (1995) 87:859). It is an RNA protein that is located in the nucleus. It has been shown that antisense to telomerase RNA inhibits the function of the enzyme and blocks the growth of cancer cells J. Feng et al., *Science,* (1995) 269:1236. RNase can also destroy the activity of telomerase. The anti-tumor protein from oocytes of Rana pipiens termed ONCONASE®, Alfacell Corporation, N.J. has homology to RNase A (Ardelt et al., 1991, *J. Biol. Chem*. 256:245–251). See also Darzynkiewicz et al. (1988) *Cell Tissue Kinet*. 21, 169–182, Mikulski et al. (1990) *Cell Tissue Kinet*. 23, 237–246. ONCONASE® destroys the activity of telomerase when incubated with a cell extract containing telomerase. It is also discovered that ONCONASE® and human RNAses such as EDN have potent anti-viral activity.

ONCONASE® is also described in U.S. Pat. No. 4,888, 172. Phase I and Phase I/II clinical trials of ONCONASE® as a single therapeutic agent in patients with a variety of solid tumors (Mikulski et aL (1993) *Int. J. of Oncology* 3, 57–64) or combined with tamoxifen in patients with advanced pancreatic carcinoma have recently been completed (Chun et al. (1995) *Proc Amer Soc Clin Oncol* 14 No. 157, 210). Conjugation of ONCONASE® to cell-type-specific ligands increased its potency towards tumor cells (Rybak et al.(1993) *Drug Delivery* 1, 3–10). ONCONASE® has properties that are advantageous for the generation of a potent selective cell killing agents; accordingly, the protein is-useful as a suicide gene as both as an anti-viral and anti-oncogenic agent. It is shown herein that low levels of expression are not cytotoxic, but do have anti-viral activity.

Modified forms of ONCONASE®, including humanized ONCONASE®, and recombinant ONCONASE® (rOnc) with a variety of activating modifications are described in copending U.S. Provisional Patent Application U.S. Ser. No. 60/011,800 filed Feb. 21, 1996 by Rybak et al. Preferred rOnc molecules have an amino terminal end selected from the group consisting of: Met-Ala; Met-Arg; Met-(J); Met-Lys-(J); Met-Arg-(J); Met-Lys; Met-Lys-Pro; Met-Lys-(J)-pro Met-Lys-(J)-Pro (SEQ ID NO:4); Met-Lys-Pro-(J) (SEQ ID NO:5 ; Met-Asn; Met-Gin; Met-Asn-(J); Met-Gln-(J); Met-Asn-(J)-Pro (SEQ ID NO:6); Met-(J)-Lys; Met-(J)-Lys-Pro (SEQ ID NO:7) and Met-(J)-Pro-Lys (SEQ ID NO:8); where (J) is Ser, Tyr or Thr. In alternative forms of the rOnc molecules, the molecules employan amino terminal end encoded by a sequence derived from the amino terminal end of EDN followed by a sequence from rOnc. In such forms, it is preferred that the amino acid sequence is one selected from the group consisting of those sequences substantially identical to those of a formula: $Met(-1)EDN_{(1-m)}Onc_{(n-104)}$; wherein Met(-1) refers to an amino terminal residue of Met; wherein $EDN_{(1-m)}$ refers to a contiguous sequence of amino acids of a length beginning at amino acid position I of EDN and continuing to and including amino acid position "m" of EDN; wherein $Onc_{(n-104)}$ refers to a sequence of contiguous amino acids beginning at amino acid position "n" and continuing to and including amino acid position 104 such that: when m is 21, n is 16 or 17; when m is 22, n is 17; when m is 20, n is 16; when m is 19, n is 15; when m is 18, n is 14; m is 17, n is 12 or 13; when m is 16, n is 11, 12, 13 or 14; when m is 15, n is 10; when m is 14; n is 9; when m is 13, n is 8; and when m is 5, n is 1. See, U.S. Ser. No. 60/011,800.

In alternative embodiments, the rOnc molecule is fused at the carboxyl end to a sequence from angiogenin. The nucleic acid sequence for human angiogenin is known.

Non-cytotoxic human members of the RNase A superfamily linked to tumor associated antigens by chemical (Rybak et al.(1991) *J. Biol. Chem* 266, 1202–21207; Newton et al. (1992) *J. Biol. Chem*. 267, 19572–19578) or recombinant means (Rybak et al. *Proc. Natl. Acad. Sci. U.S.A*. 89, 3165, Newton et al. (1994) *J Biol Chem*. 269, 26739–26745) offer a strategy for selectively killing tumor cells with less concomitant immunogenicity than current strategies which employ plant and bacterial toxins provide. See also, Rybak, S. M. & Youle, R. J. (1991) *Immunol. and Allergy Clinics of North America* 11:2, 359–380. Human-derived ribonucleases of interest include eosinophil-derived neurotoxin (EDN) and angiogenin. It is surprisingly discovered that EDN has anti-HIV activity.

(ii) Antisense Genes

An antisense nucleic acid is a nucleic acid that, upon expression, hybridizes to a particular mRNA molecule, to a transcriptional promoter, or to the sense strand of a gene. By hybridizing, the antisense nucleic acid interferes with the transcription of a complementary nucleic acid, the translation of an mRNA, or the function of a catalytic RNA. Antisense molecules useful in this invention include those that hybridize to HIV genes and gene transcripts. Chatterjee and Wong, (1993) *Methods, A companion to Methods in Enzymology* 5: 51–59 and Marcus-Sekura (*Analytical Biochemistry* (1988) 172, 289–285) describe the use of antisense RNA to block or modify gene expression.

(iii). Ribozymes

A ribozyme is a catalytic RNA molecule that cleaves other RNA molecules having particular nucleic acid sequences. Ribozymes useful in this invention are those that cleave HIV gene transcripts. Ojwang et al. (1992) *Proc. Nat'l. Acaci Sci., U.S.A*. 89:10802–10806 provide an example of an HIV-1 pol-specific hairpin ribozyme.

(iv). Decoy Nucleic Acids

A decoy nucleic acid is a nucleic acid having a sequence recognized by a regulatory nucleic acid binding protein (i.e., a transcription factor). Upon expression, the transcription factor binds to the decoy nucleic acid, rather than to its natural target in the genome. Useful decoy nucleic acid sequences include any sequence to which a viral transcription factor binds. For instance, the TAR sequence, to which the Tat protein binds, and HIV RRE sequence, to which the Rev proteins binds are suitable sequences to use as decoy nucleic acids. Thus, most gene therapy vectors containing the HIV LTRs of the present invention serve as decoy nucleic acids.

Examples of antisense molecules, ribozymes and decoy nucleic acids and their use can be found in Weintraub (Jan. 1990) *Sci. Am.* 262:40–46; Marcus-Sekura (1988) *Anal. Biochem.* 172:289–95; and Hasselhoff et al. (1988) *Nature* 334:585–591.

(v). Transdominant Proteins

A transdominant protein is a protein whose phenotype, when supplied by transcomplementation, will overcome the effect of the native form of the protein. For example, tat and rev can be mutated to retain the ability to bind to TAR and RRE, respectively, but to lack the proper regulatory function of those proteins. See, e.g., Nabel et al. (1994) *Human Gene Therapy* 5:79–92. For example, rev can be made transdominant by eliminating the leucine-rich domain close to the C terminus which is essential for proper normal regulation of transcription. Tat transdominant proteins can be generated by mutations in the RNA binding/nuclear localization domain. A comparison of the effects of trans dominant Tat and Rev is found in Bahner et al. (1993) *Journal of Virology* 67(6): 3199. Delta-gag has been shown to inhibit HIV-1 replication, presumably by interfering with viral assembly (Trono, et al., *Cell*, 59, 113–120 (1989); Lori, et al., *Gene Therapy*, 1, 27–31 (1994)).

(vi). Suicide Genes

A suicide gene produces a product which is cytotoxic. In the gene therapy vectors of the present invention, a suicide gene is operably linked to an expression control sequence in the vector which is stimulated upon infection by HIV (e.g., an LTR which requires Tat for activation in a vector which does not encode tat). Upon infection of the cell by competent virus, the suicide gene product is produced, thereby killing the cell and blocking replication of the virus. In addition to high levels of ONCONASE®, suicide genes can include essentially any gene which is cytotoxic, coupled with a promoter which directs expression only in virally infected cells, or in tumor cells.

Targeting Vectors

Vectors are targeted by a variety of means known in the art. In one preferred class of embodiments, the vectors of the invention include retroviral particles. These particles are typically specific for cell types within the host range of the retrovirus from which the particle is derived. For example, HIV infects CD4+ cells; accordingly, in one preferred embodiment, the vectors of the invention comprise an HIV particle, enabling the vector to be transduced into CD4+ cells, in vitro, ex vivo or in vivo. Vectors comprising HIV particles can also be used to transduce non-dividing hematopoietic stem cells (CD34+), by pseudotyping the vector. CD34+ cells are a good target cells for ex vivo gene therapy, because the cells differentiate into many different cell types, and because the cells re-engraft into a patient undergoing ex vivo therapy. The vesicular stomatitis virus envelope glycoprotein (VSV-G) has been used to construct VSV-G-pseudotyped HIV vectors which can infect hematopoietic stem cells (Naldini et al. (1996) *Science*, 272:263 and Akkina et al. (1996) *J Virol* 70:2581). Additional methods of transferring nucleic acids into CD34+ hematopoietic progenitor cells are described in Brenner (1993) *Journal of Hematotherapy* 2: 7–17.

In addition to viral particles, a variety of protein coatings can be used to target nucleic acids to selected cell types. Transferrin-poly-cation conjugates enter cells which comprise transferrin receptors. See, e.g., Zenke et al (1990) *Proc. Natl. Acad. Sci. USA* 87: 3655–3659; Curiel (1991) *Proc. Natl. Acad Sci USA* 88: 8850–8854 and Wagner et al. (1993) *Proc. Natl. Acad. Sci. USA* 89:6099–6013.

Naked plasmid DNA bound electrostatically to poly-1-lysine or poly-1-lysine-transferrin which has been linked to defective adenovirus mutants can be delivered to cells with transfection efficiencies approaching 90% (Curiel et al. (1991) *Proc Nail Acad Sci USA* 88:8850–8854; Cotten et al. (1992) *Proc Natl Acad Sci USA* 89:6094–6098; Curiel et al. (1992) *Hum Gene Ther* 3:147–154; Wagner et al. (1992) *Proc Natl Acad Sci USA* 89:6099–6103; Michael et al. (1993) *J Biol Chem* 268:6866–6869; Curiel et al. (1992) *Am J Respir Cell Mol Biol* 6:247–252, and Harris et al. (1993) *Am J Respir Cell Mol Biol* 9:441–447). The adenovirus-poly-1-lysine-DNA conjugate binds to the normal adenovirus receptor and is subsequently internalized by receptor-mediated endocytosis. The adenovirus-poly-1-lysine-DNA conjugate binds to the normal adenovirus receptor and is subsequently internalized by receptor-mediated endocytosis. Similarly, other virus-poly-1-lysine-DNA conjugates bind the normal viral receptor and are subsequently internalized by receptor-mediated endocytosis. Accordingly, a variety of viral particles can be used to target vector nucleic acids to cells.

Other receptor-ligand combinations which can be used to target DNA which is complexed to the ligand to a cell include cytokines and cytokine receptors, interleukins and interleukin receptors, c kit and the c kit receptor (see, Schwartzenberger et al (1996) *Blood* 87: 472–478), antibodies and cell surface molecules, and the like.

In addition to, or in place of receptor-ligand mediated transduction, the vector nucleic acids of the invention are optionally complexed with liposomes to aid in cellular transduction. Liposome based gene delivery systems are described in Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Nail. Acad. Sci. USA* 84:.7413–7414.

Promoters

The particular promoter used to direct expression of the viral and oncogenic inhibitors of the invention depends on the particular application. A variety of promoters are known, and no attempt is made to catalogue the wide variety of promoters which can be used to direct expression of inhibitors in the constructs of the invention. Promoters are typically selected to provide selective expression of the viral inhibitor or inhibitors when the inhibitors are needed to inhibit viral production in a cell, or to inhibit tumor growth. For example, HIV LTRs provide convenient promoters which direct high levels of expression in the presence of Tat. Thus, inhibitors of HIV are optionally placed under the regulatory control of an HIV LTR promoter, which is activated upon infection of the cell by an HIV. Similarly, the probasin promoter is active in prostate cells, providing a convenient means of targeting prostate tumor inhibitor expression to prostate cells. See, Greenberg et al. (1994) *Mol Endocrinol* 8: 230–239.

Constitutive promoters are also appropriate in certain contexts. For example, where the vector of the invention is targeted to a tumor cell, an inhibitory cytotoxic gene such as ONCONASE (or other ribonucleases from the pancreatic ribonuclease A superfamily, such as EDN or angiogenin) can be placed under the control of a strong constitutive promoter such as the CMV promoter. Since the vector is only transduced into target cells, and since the cells are to be killed by the inhibitor, a high level of expression is desirable. When cell killing is desired, high levels of expression of multiple RNAses by the vector of the invention is a preferred embodiment.

Optimization of Expression of Multicistronic Messages

Multicistronic messages include an upstream promoter and open reading frame and a downstream open reading frame under the control of the same promoter. Both open reading frames are encoded by the same mRNA. Translation of the downstream open reading frame depends on the ability of the ribosome to reinitiate at the internal start codon of the downstream open reading frame. Levine et al. (1991) *Gene* 167–174 describe some of the considerations which affect expression of multicistronic messages. One factor is the intercistronic distance; short intercistronic distances inhibit reinitiation; typically the distance between open reading frames is about 10–500 bp. In some embodiments, the distance between open reading frames is about 20–200 bp. In other embodiments, the distance between open reading frames is about 30–100 bp.

A second factor is the presence or absence of a Kozak consensus sequence surrounding the start site of downstream messages. The absence of a Kozak sequence decreases the level of expression for downstream open reading frames.

The encephalomyocarditis virus internal ribosome entry site (IRES) described, e.g., by Ghattas et al. (1991) *Molecular and Cellular Biology* 5848–5859, provides for more efficient expression of downstream open reading frames, particularly when the downstream open reading frame comprises a Kozak sequence and the spacing between the IRES and the downstream open reading frame is optimized. However, an IRES is not required for downstream translation initiation.

Optimizing expression from downstream viral inhibitors depends on the application. In some applications, high levels of expression from the downstream viral inhibitors (or other elements of the vectors of the invention, such as reporter genes) are desirable. In these applications, the downstream open reading frames comprise a Kozak sequence, an IRES is used, and the distance between the IRES and downstream open reading frames is optimized for maximum translational efficiency. This optimization is performed by making several constructs with varying intercistronic (or IRES-open reading frame) distances and assaying for translation products in cell culture (e.g., by western blot or ELISA analysis).

In other applications, the level of expression is preferably low, to avoid side effects and cellular toxicity. For example, pBAR-EDN and p-BAR-ONC described herein lack a Kozak sequence, making the level of expression of EDN and ONCONASE low in these constructs. This low level of expression inhibited HIV in transformed cells, without the cytotoxicity observed in cells expressing high levels of, e.g., ONCONASE.

Reporter genes, Sites of Replication and Selectable Markers

To monitor the progress of cellular transduction, a marker or "reporter" gene is optionally encoded by the vector nucleic acids of the invention. The inclusion of detectable markers provides a means of monitoring the infection and stable transduction of target cells. Markers include components of the beta-galactosidase gene, the firefly luciferase gene and the green fluorescence protein (see, e.g., Chalfie et al. (1994) *Science*, 263:802).

The vectors of the invention optionally include features which facilitate the replication in more than one cell type. For example, the replication of a plasmid as an episomal nucleic acid can be controlled by the large T antigen in conjunction with an appropriate origin of replication, such as the origin of replication derived from the BK papovavirus. Many other features which permit a vector to be grown in multiple cell types (e.g., shuttle vectors which are replicated in prokaryotic and eukaryotic cells) are known.

Selectable markers which facilitate cloning of the vectors of the invention are optionally included. Sambrook and Ausbel, both supra, provide an overview of selectable markers.

Cellular Transformation

The present invention provides nucleic acids for the transformation of cells in vitro and in vivo. These packageable nucleic acids are packaged, e.g., in HIV particles. The packageable nucleic acids are transfected into cells through the interaction of the HIV particle surrounding the nucleic acid and the HIV cellular receptor. Cells which are transfected by HIV particles in vitro include CD4+ cells, including T-cells such as Molt-4/8 cells, SupT1 cells, H9 cells, C8166 cells and myelomonocytic (U937) cells as well as primary human lymphocytes, and primary human monocyte-macrophage cultures, peripheral blood dendritic cells, follicular dendritic cells, epidermal Langerhans cells, megakaryocytes, microglia, astrocytes, oligodendroglia, CD8+ cells, retinal cells, renal epithelial cells, cervical cells, rectal mucosa, trophoblastic cells, and cardiac myocytes (see also, Rosenburg and Fauci Rosenburg and Fauci (1993) in *Fundamental Immunology, Third Edition* Paul (ed) Raven Press, Ltd., New York). Thus, the packageable nucleic acids of the invention are generally useful as cellular transformation vectors.

In one particularly preferred class of embodiments, the packageable nucleic acids of the invention are used in cell transformation procedures for gene therapy. Gene therapy provides methods for combating chronic infectious diseases such as HIV, as well as non-infectious diseases such as cancer and birth defects such as enzyme deficiencies. Yu et al. (1994) *Gene Therapy* 1:13–26 and the references therein provides a general guide to gene therapy strategies for HIV infection. See also, Sodoski et al. PCT/US91/04335. The present invention provides several features that allow one of skill to generate powerful retroviral gene therapy vectors which specifically target CD4+ and CD34+ cells in vivo, and which transform many cell types in vitro. CD4+ cells, including non-dividing cells, are transduced by nucleic acids packaged in HIV particles. HIV particles also infect other cell-types in vitro which exhibit little or no CD4 expression, such as peripheral blood dendritic cells, fowcular dendritic cells, epidermal Langerhans cells, megakaryocytes, microglia, astrocytes, oligodendroglia, CD8+ cells, retinal cells, renal epithelial cells, cervical cells, rectal mucosa, trophoblastic cells, and cardiac myocytes (see, Rosenburg and Fauci 1, supra). Thus, these cells can be targeted by the HIV particle-packaged nucleic acids of the invention in ex vivo gene therapy procedures (the infection of these cell types by HIV in vivo, however, is rare), or in drug discovery assays which require transformation of these cell types. Lists of CD4+ and CD4- cell types which are infectible by HIV have been compiled (see, Rosenburg and Fauci supra; Rosenburg and Fauci (1989) *Adv Immunol* 47:377–431; and Connor and Ho (1992) in *AIDS: etiology, diagnosis,* treatment, and prevention, third edition Hellman and Rosenburg (eds) Lippincott, Philadelphia).

Ex Vivo Transduction of Cells

Er vivo methods for inhibiting viral replication in a cell in an organism involve transducing the cell ex vivo with a therapeutic nucleic acid of this invention, and introducing the cell into the organism. The cells are typically CD4+ cells such as CD4+ T cells, or are macrophage isolated or cultured from a patient, or are stem cells. Alternatively, the cells can be those stored in a cell bank (e.g., a blood bank).

In one class of embodiments, the vectors of the invention inhibit viral replication in cells already infected with HIV virus, in addition to conferring a protective effect to cells which are not infected by HIV. In addition, in one class of embodiments, the vector is replicated and packaged into HIV capsids using the HIV replication machinery, thereby causing the anti-HIV inhibitor to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides compositions and methods for protecting cells in culture, ex vivo and in a patient, even when the cells are already infected with the virus against which protection is sought.

The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells. Transduced cells are cultured by means well known in the art. See, also Kuchler et al. (1977) *Biochemical Methods in Cell Culture and Virology*, Kuchler, R. J., Dowden, Hutchinson and Ross, Inc. Mammalian cell systems often will be in the form of monolayers of cells, although mammalian cell suspensions are also used. Illustrative examples of mammalian cell lines include VERO and Hela cells, Chinese hamster ovary (CHO) cell lines, W138, BHK, Cos-7 or MDCK cell lines (see, e.g., Freshney, supra).

In one embodiment, CD34+ stem cells (which are typically not CD4+) are used in ex-vivo procedures for cell transduction and gene therapy. The advantage to using stem cells is that they can be introduced into a mammal (such as the donor of the cells) where they will engraft in the bone marrow.

In humans, CD34+ cells can be obtained from a variety of sources including cord blood, bone marrow, and mobilized peripheral blood. Purification of CD34+ cells can be accomplished by antibody affinity procedures. An affinity column isolation procedure for isolating CD34+ cells is described by Ho et al. (1995) *Stem Cells* 13 (suppl. 3): 100–105. See also, Brenner (1993) *Journal of Hematotherapy* 2: 7–17. Yu et al. (1995) PNAS 92: 699–703 describe a method of transducing CD34+ cells from human fetal cord blood using retroviral vectors.

Rather than using stem cells, T cells are also used in some embodiments in ex vivo procedures. Several techniques are known for isolating T cells. The expression of surface markers facilitates identification and purification of T cells.

Methods of identification and isolation of T cells include FACS, incubation in flasks with fixed antibodies which bind the particular cell type and panning with magnetic beads. One procedure for isolating T cells is described in Leavitt et al. *Hum. Gene Ther.* (1994) 5:1115–1120.

Administration of Vectors and Transduced Cells

Vectors, transduced cells and vector nucleic acids can be administered directly to a patient for transduction of cells in the patient. Administration is by any of the routes normally used for introducing a molecule into ultimate contact with blood or tissue cells. Vector packaged nucleic acids of the invention are administered in any suitable manner, preferably with pharmaceutically acceptable carriers. Alternatively, the nucleic acids can be naked, or present in a liposome. Suitable methods of administering such nucleic acids in the context of the present invention to a patient are available.

Pharmaceutically acceptable excipients are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are suitable methods of administration. The formulations of packaged nucleic acid can be presented in unit-dose or multi-dose sealed containers, such as ampules and vials.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of virally-mediated diseases such as AIDS, the physician evaluates circulating plasma levels, vector and ribozyine toxicities, progression of the disease, and the production of anti-vector antibodies.

For administration, vectors and transduced cells of the present invention can be administered at a rate determined by the LD-50 of the vector, or transduced cell type, and the side-effects of the vector or cell type at various concentrations, as applied to the mass and overall health of the patient. Administration can be accomplished via single or divided doses. For a typical 70 kg patient, a dose equivalent to approximately 0.1 $\mu$g to 10 mg are administered.

Transduced cells are optionally prepared for reinfusion according to established methods. See, Abrahamsen et al. (1991) *J. Clin. Apheresis* 6:48–53; Carter et al. (1988) *J. Clin. Apheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. In one class of ex vivo procedures, between $1 \times 10^6$ and $1 \times 10^9$ transduced cells (e.g., stem cells or T cells transduced with vectors encoding the ribozymes of the invention) are infused intravenously, e.g., over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion may be repeated about every 2 to 3 months for a total of 4 to 6 treatments in a one year period. After the first treatment, infusions can be performed on a outpatient basis at the discretion of the clinician.

If a patient undergoing infusion of a vector or transduced cell develops fevers, chills, or muscle aches, he/she typically receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

The effect of the therapeutic vectors or transduced cells of the invention on HIV infection and AIDS are measured by monitoring the level of HIV virus in a patient, or by monitoring the CD4+ cell count for the patient over time. Typically, measurements are taken before, during and after the therapeutic regimen. Kits for detecting and quantitating HIV, and CD4+ cells are widely available. Virus and CD4+ cells can be detected and quantified using an immunoassay such as an ELISA, or by performing quantitative PCR. Cell sorting techniques such as FACS are often used to isolate and quantify CD4+ cells.

EXAMPLES

The following examples are provided by way of illustration only and not by way of limitation. Those of skill will readily recognize a variety of noncritical parameters which can be changed or modified to yield essentially similar results.

Example 1

Complete Inhibition of HIV-J Replication by Combined Expression of a Gag Dominant Negative Mutant And a Human Ribonuclease in a Tightly Controlled HIV-1 Inducible Vector This example provides HIV-1 based expression vectors which produce protective genes tightly regulated by HIV-1 Tat and Rev proteins. The vector contains either a single protective gene (HIV-1 Gag dominant negative mutant [delta-Gag]) or a combination of two different protective genes (delta-Gag and eosinophil-derived neurotoxin [EDN], a human ribonuclease) expressed from a dicistronic mRNA. After stable transfection of CEM T cells and following challenge with HIV-1, viral production was completly inhibited in cells transduced with the vector producing both delta-Gag and EDN and partially inhibited in cells producing delta-Gag alone. In addition, the expressed mRNA, containing the packaging signal o HIV-1, was incorporated into the HIV-1 virion along with the viral genomic mRNA, as shown after co-transfection into HeLa-Tat cells of an infectious molecular clone and either vector carrying the protective genes. Following infection of peripheral blood lymphocytes with viruses containing both RNAS, the mRNA for the protective gene was reverse transcribed into newly infected cells, thus transmitting protection throughout the target cells.

Expression vectors. Vectors were constructed by insertion of the protective genes into pRBK (Invitrogen, San Diego, Calif.), an episoma mammalian expression plasmid vector, the replication of which is driven by the large T antigen and the origin of replication of BK papovavirus. For the construction of pBAR, the 5' LTR from HIV-1 molecular clone pLW/C (Cara, et al., *J. Biol. Chem.*, 271, 5393–5397 (1996)) and delta-Gag from a plasmid containing a dominant negative gag gene (Lori, et aL, *Gene Therapy*, 1, 27–31 (1994)) were amplified using the primers pair SU3/EU5AS and EU5S/XDGAS, respectively, with Vent DNA polymerase (New England Biolabs, Beverly, Mass.) following the manufacturer's instructions. The delta-gag gene was provided with two stop codons (see, the oligonucleotide sequences herein) to ensure termination of transcription. At the junction between the LTR and delta-gag an EcoRI site which does not disrupt either the primer binding site or the major splicing donor was inserted. After EcoRI digestion, PCR products were ligated together and purified on an agarose gel. Following SmaI/XbaI digestion, the LTR-delta-gag fragment was cloned into the SmaI/NheI sites of the Bluescript II SK-plasmid (Stratagene, La Jolla, Calif.). A DNA fragment containing the RRE and 3' LTR (derived from the widely available HXB2 molecular clone of HIV-1) was amplified from the pCgagA2 plasmid with Vent DNA polymerase using the primer pair SRRES/BLU5AS and inserted into the XhoI/BamHI sites of the pRBK plasmid. The pRBK-containing RRE plasmid was digested with XhoI/SacII and the DNA fragment containing the RRE-LTR DNA fragment and the SV40 polyadenylation signal (SV40pA) derived from the pRBK plasmid was subcloned into the SalI/SacII sites of the Bluescript plasmid containing the LTR-delta-gag DNA fragment, thus obtaining the PBS-BAR. Clone pBS-BAR was digested with SmaI/SacII and inserted into the SmaI/SacII sites of the pRBK plasmid to obtain the pBAR plasmid.

For the construction of pBAR-EDN, the PET/EDN plasmid (Newton, et al., *J. BioL Chem.*, 269, 26739–26745 (1994)) containing the entire coding sequence of EDN was digested with XbaI/BamHI and subcloned in Bluescript previously digested with XbaI/BamHI to obtain the pEDN plasmid. The IRES sequence was amplified from the pLZIN plasmid (Ghattas, et al., *Mol. Cell. Biol.*, 11, 5848–5859 (1991)) using Vent DNA polymerase and the oligonucleotide primers pair IRESA/IRESB. After amplification, the PCR product containing the IRES sequence was digested with XbaI/SpeI and subcloned into pEDN previously digested with XbaI to obtain the pIREDN plasmid. pIREDN was then digested with EcorV and into this site was inserted a NotI linker to obtain the plasmid pIREDNN. pIREDNN was digested with NotI and the insert containing the IRES and EDN sequences was inserted into the NotI site of the pBAR plasmid between the delta-gag gene and RRE sequences to obtain the pBAR-EDN plasmid. For the construction of pBS-BAR-luc, a NotI/BamHI DNA fragment containing the IRES sequence was placed in front of the luciferase gene into the NotI/BamHI restriction sites of the pGEM-luc vector (Promega, Madison, Wis.) to obtain the plasmid pIRES-luc. After digestion of pIRES-luc with EagI, the DNA fragment containing the IRES-luciferase was subcloned into the NotI site of PBS-BAR to obtain the pBS-BAR-luc plasmid. The expression plasmid for Tat, pRBK-Tat, has been previously described (Cara, et al., *J. Biol. Chem.*, 271, 5393–5397 (1996)). The Rev expression plasmid, pRBKRev, consists of the rev gene cloned into the BamHI site of the pRBK plasmid. Transcription of tat and rev is driven by the RSV promoter.

CEM transfection and selection. Plasmids pBAR, pBAR-EDN, and pRBK were introduced by electroporation into the CEM T cell line (10 μg DNA per 2.5×10⁷ cells, 200 mV, 960 μF). Seventy-two hours after transfection, cells were cultured in RPMI medium with 10% fetal calf serum (FCS) and 800 μg ml⁻¹ hygromycin B (Boehringer, Indianapolis, Ind.). One month after the selection, transduced cells showed normal growth characteristics compared to the parental cell line and greater than 95% of the cells were CD4+.

DNA transfection. The human epithelial HeLa and HeLa-Tat cell lines were maintained in Dulbecco's modified Eagle medium (DMEM) supplemented with 10% fetal calf serum (FCS). For transfection experiments, equimolar amounts of plasmid DNA (up to a total of 30 μg) were introduced into Hela or HeLa-Tat cells using the Calcium Phosphate method (ProFection Mammalian Transfection System, Promega). Thirty six or forty eight hrs after transfections, supernatants were analyzed for RT activity, p24 production and viral RNA. Cell lysates were also analyzed for p55$^{delta-gag}$, luciferase activity or EDN content or for RNA.

Southern blot hybridization. Plasmid DNA in the transduced cell cultures were assayed by Southern blot hybridization after DNA extraction using the Hirt method (Hirt, B., *J. Mol. Biol.* 26, 365–369 (1967)). Briefly, after extraction, DNA was digested with EcoRI, separated on an 1% agarose gel, blotted onto Nytran filters (Schleicher and Schuell, Keene, N.H.) and hybridized in 7% SDS (Church, et al., *Proc. Natl. Acad. Sci. USA*, 81, 1991–1995 (1984)) with ³²p-labelled pRBK-EDN. Detection of the DNA bands of the correct size was verified by concurrent digestion of the parental plasmids.

RNA extraction and analysis. Total cellular RNA was extracted using TRIzol reagent (Life Technologies, Gaithersburg, Md.) and resuspended in formammide. For northern blot analysis, 10 μg of RNA were loaded on a formaldehyde denaturing agarose gel. After electrophoresis, RNA was transferred onto a Nytran filter (Schleicher and Schuell) and hybridized with a 32p labelled complete HIV-1 $_{LW/C}$ LTR (which recognizes all the messenger RNAs expressed from these constructs) or IRES sequences (which hybridizes only to the RNA transcribed from pBAR-EDN) as previously described (Cara, et al., *Cell. Mol. Neurobiol.*, 12, 131–142 (1992)). For analysis of packaged virion RNA, supernatants derived from the transfections were extracted directly from the transfected HeLa-Tat cells after low speed centrifugation and filtration, using TRIzol LS reagent (Life Technologies). Following DNase treatment and phenotchloroform-isoamyl alcohol extraction, samples were spotted on a Nytran filter (Schleicher & Schuell). Filters were hybridized using a fragment of DNA containing either the HIV-1 $_{LW/C}$ LTR, the IRES sequence or the ampicillin gene and, after extensive washing, autoradiographed for forty-eight hours.

Western blot anatysis. Cells were lysed in absolution containing Tris-HCl pH 7.4 50 mM, NaCl 150 MM, NP40 0.5%, NaF 50 mM, PMSF 1mM, Na₃VO₄ 1mM, leupeptine 25 μg/ml, aprotinin 25 μg/ml and trypsin inhibitor 10 μg/ml. Equal amounts of total proteins were loaded on a 10% SDS-PAGE gel, transferred to nitrocellulose membrane and incubated with a rabbit polyclonal antibody against p24 (Program Resources Inc., NCI, FCRDC, Frederick, Md.). Cheminuminescent detection of blotted proteins was performed using the ECL kit (Amersham, Arlington Heights, Ill.).

Cell culture and HIV-1 infection. Transduced CEM cells were cultured in RPMI 1640 supplemented with 10% FCS and 800 μg ml⁻¹ hygromycin B (Boehringer). For infections, cells were incubated with HIV-1$_{UIB}$, at the estimated multiplicity of infection (MOI) indicated in the text. After 2 hours of incubation, cells were washed three times and incubated in tissue culture flasks at a density of 0.5×106 per milliliter. Collection of the supernatants for viral RT and p24 analysis and of cells for DNA analysis together with measurements of viability and cell surface CD4 were carried out twice a week. For RNA analysis, cells were harvested every other day for the first week after infection. Peripheral blood lymphocytes (PBLs) were derived from healthy donors by separation with Ficoll gradient centrifugation. PBLs were cultured for 72 hrs in RPMI complete medium with 10% fetal calf serum (FCS) in the presence of 2 μg/mi of purified phytohemagglutinin (Sigma, St. Louis, Mo.) and 10 U/ml of interleukin 2. For infection experiments, PBLs were infected with normalized amounts of virus derived from co-transfection of either pHXB2/pRBK or pHXB2/pBAR-EDN.

RT assay and p24 ELISA. RT assays were performed by standard procedures. Production of p24 was analyzed using a p24 antigen capture ELISA kit (Coulter Corp., Miami, Fla.).

Luciferase assay. HeLa cells were transfected using the Calcium Phosphate method with 1 μg of reporter plasmid DNA ILTR-luc-LTR-Circle (which contains the firefly luciferase gene downstream a complete HIV-1 $_{LW/C}$ LTR [Cara, et al., *J. Biol. Chem.*, 271, 5393–5397 (1996)]), pGEM-luc (Promega) or pBS-BAR-luc. A 2 to 1 molar ratio of pRBK-Rev and pRBK-Tat plasmid were co-transfected along with the reporter plasmid. Forty-eight hours after transfection, cells were lysed in a solution containing 1% triton x-100, 2 mM DTT, 25 MM Tris, pH 7.8, 2 mM CDTA, 10% glycerol and analyzed for luciferase activity using a Bertholdt luminomcter.

PCR anatsis. DNA was extracted using the Urea lysis method. Briefly, cells were lysed in a solution containing 7M urea, 0.3M NaCl, 10mM Tris-Cl pH 8.0, 10mM EDTA pH 8.0 and 1% SDS and incubated at 65° C. for two hours. Samples were phenolchloroform extracted and resuspended in water after 70% ethanol washes. PCR amplification was performed depending on the primer pair used. Primers βGS/βGAS and condition used for amplification of β-globin have been described (Cara, et al., *Virology*, 208, 242–248 (1995)). After normalization, 10 ng of DNA and primers ENVA/ENVB were used to amplify the envelope (env) region of HIV-1. The conditions for amplification were: 1 min at 94° C. (denaturation), 1 min at 60° C. (annealing) and 1 min at 72° C. (extension) for 30 cycles. For detection of the amplified envelope fragments, primer ENVC was used after T4-PNK end-labelling. Primers 516/477 were used to amplify the 2-LTR circular form of HIV-1 in the region spanning the junction between the two LTRs (U5-U3) for 40 cycles as described (Cara, et al., *Virology*, 208, 242–248 (1995)) using 20 ng of DNA. The probe was oligonucleotide 569F. For RT-PCR, RNA was extracted from 1×10⁶ peripheral blood lymphocytes (PBLs) using TRIzol reagent. After extraction, contaminating DNA was digested with DNase, RNase-free (Boehringer). RNA was reverse transcribed using AMV RT (Promega) as previously described (Cara, et al., *Cell. Mol. Neurobiol.*, 12, 131–142 (1992)) and amplified using primer pair EDNα/EDNω, to detect the RNA codifying for the EDN gene, or ECOSPL/OTESAPL, to detect the 0.8 kb spliced mRNA transcribed from pBAR-EDN in the absence of Tat and Rev. For hybridization a fragment of DNA containing the coding sequence of EDN and oligonucleotides EU5S respectively were used. Conditions for cDNA amplification using either primer pair were: 1 min at 94° C., 1 min at 60° C. and 1 min at 72° C. for 36 cycles. For the standard curve (stds DNA), serial dilutions of a plasmid containing the same region which was amplified were used. As external controls for β-globin amplification, serial dilutions of known amounts of genomic DNA were used. All PCR products were blotted and analyzed onto 0.2 μm pore size Nytran membranes (Schleicher & Schuell) using standard methods (Sambrook, et al., *Molecular Cloning*, Cold Spring Harbor Laboratory Press, Cold Spring Harbor, N.Y. (1989)).

Oligonucleotides.

SU3: 5'-AAAAGGCCTCCCGGG ACTGGAAGGGCTAATTCACT-3' (SEQ ID NO:9). The bases corresponding to nt. 16–35 in the LW/C viral sequence are underlined; the SmaI site is bold; sense orientation.

EU5AS: 5'-CCGGAATTC ACCAGTCGCCGCCCCTCGCC-3' (SEQ ID NO:10). The bases corresponding to nt. 744–763 in the LW/C viral sequence are underlined; the EcoRI site is bold; antisense orientation.

EU5S: 5'-CCGGAATTC GCCAAAAAATTTTGACTAGCG-3' (SEQ ID NO:11). The bases corresponding to nt. 770–790 in the LW/C viral sequence are underlined; the EcoRI site is bold; sense orientation.

XDGAS: 5'-GGATCTAGATCTAGA TTGCCCCCCTATCATTATTGT-3' (SEQ ID NO: 12). The bases corresponding to nt. 2284–2305 in the HXB2 viral sequence are underlined; the XbaI sites are bold; the stop codons are double underlined; antisense orientation.

SRRES: 5'-GGACGCGTCGAC ACCATTAGGAGTAGCACCCAC-3' (SEQ ID NO: 13). The bases corresponding to nt. 7698–7717 in the HXB2 viral sequence are underlined; the SalI site is bold; sense orientation.

BLU5AS: 5'-CGCGGATCC ACTGACTAAAAGGGTCTGAG-3' (SEQ ID NO:14). The bases corresponding to nt. 9681–9700 in the HXB2 viral sequence are underlined; the BamHI site is bold; antisense orientation.

ENVA: 5'-AGAAATATCAGCACTTGTGGAGA-3' (SEQ ID NO:15). The sequence corresponds to nt. 6237–6259 in the HXB2 viral sequence; sense orientation.

ENVB: 5'-TGAGTGGCCCAAACATTATGTACCT-3' (SEQ ID NO:16). The sequence corresponds to nt. 6414–6438 in the HXB2 viral sequence; antisense orientation.

ENVC: 5'-CACCACTCTATTTTGTGCATCAGATG-3' (SEQ ID NO:17). The sequence corresponds to nt. 6369–6395 in the HXB2 viral sequence; sense orientation.

IRESA: 5'-GCTCTAGAGGAATTCCGCCCCTC-3' (SEQ ID NO:18) The XbaI site is bold; the EcoRI site is underlined; sense orientation (5' of the sequence).

IRESB: 5'-GACTAGTGGCAAGCTTATCATCGTG-3' (SEQ ID NO:19). The SpeI site is bold; antisense orientation (3' of the sequence).

EDNα: 5'-CGCGGATCCTTGATATGCTGAGTTTCGAACCA-3' (SEQ ID NO:20). Sense orientation.

EDNω: 5'-AAGGAAAAAAGCGGCCGCCTACTAGATGATA CGGTCCAGA-3' (SEQ ID NO:21). Antisense orientation.

ECOSPL: 5'-GGGCGGCGACTGGTGAATT-3' (SEQ ID NO:22). Corresponding to nt. 750–768 in the pLW/C sequence. The nucleotides in bold correspond to the mutated nucleotides, with respect to pLW/C, present in pBAR and pBAR-EDN plasmids after the introduction of the EcoRI site. Sense orientation.

OTESAPL: 5'-TCTAACACTTCTCTCTCCGGGT-3' (SEQ ID NO:23). Corresponding to nt. 9317–9339 in the pHXB2 sequence. Antisense orientation. Oligonucleotides 516, 477, 569F, βGS and βGAS have been described (Cara, et al., *Virology*, 208, 242–248 (1995)).

Regulation of HIV-1 based vectors. Different features which allow control of the expression both at the transcriptional and RNA processing levels by the early regulatory HIV-1 proteins Tat and Rev were included in the vectors pBAR and pBAR-EDN (FIG. 1) in order to obtain a tight and complete responsiveness to Tat and Rev. To test the regulatory role of Tat and Rev on the expression of vectors pBAR, PBAR-EDN and the control plasmid pRBK, each construct was transfected into HeLa cells either alone or in combination with vectors expressing Tat and Rev under the control of the RSV promoter. Thirty-six hours following the transfection, RNA was isolated and Northern analysis was performed using HIV-1 LTR as a probe to determine the expression levels of the different constructs. In the absence of Tat and Rev, low steady state levels of a 0.8 Kb mRNA were detected, indicating a basal transcriptional activity independent of Tat and Rev. The basal activity is driven by the low constitutive activation of the HIV-1 LTR as previously reported (Bohan, et al., *Gene Expr*. 2, 391–407 (1992). As expected, no signal from the control transfection with pRBK was observed.

A 0.8 Kb mRNA representing the fully processed form that originates from splicing between the major splice donor site 5' of the gag gene and a splice acceptor site located in the 3' LTR (Smith, et al., *J. Gen. Virol.*, 73, 1825–1828 (1992)) was observed. Under these conditions the full length mRNA remained undetectable, indicating that, in the absence of Tat and Rev, all the transcripts deriving from the basal activity of HIV-1 LTR were processed to a mature form which did not contain any of the protective genes. Therefore, this processing mechanism prevented the production of the protective proteins in the absence of HIV-1 infection.

However, when Tat and Rev were provided in trans by cotransfection, a the mRNA corresponding to the complete size of the transcriptional units for each plasmid were readily detected at abundant levels. On the other hand, the 0.8 Kb band, corresponding to the spliced mRNA, became almost undetectable. These data demonstrated that indeed Tat and Rev act on the activation of the transcription and on the processing of the full length mRNA, respectively. HeLa cells transfected with pRBK plasmid were used as negative control and did not show any signal. Accordingly, $p55^{delta-gag}$ protein was detected by both ELISA and Western blot analysis only in HeLa cells transfected with either pBAR or pBAR-EDN along with Tat and Rev expressing plasmids. Lower amounts of $p55^{delta-gag}$ were detected after transfection of pBAR-EDN compared to pBAR.

Expression of EDN was also analyzed after HeLa transfection with pBAR and pBAR-EDN alone or together with Tat and Rev expressing plasmids. To minimize the possibility that the expression of EDN would lead to cell death in the presence of Tat and Rev, the gene was inserted between the IRES and RRE sequences without its Kozak consensus sequence, a sequence which is generally required for optimal translation of eukaryotic mRNAs (Kozak, M., *J. Cell. Biol.*, 108, 229 (1989)). Western blot analysis failed to detect any signal for EDN protein in the same cellular extract where $p55^{delta-gag}$ was detected. To check for proper functionality of IRES sequence, the EDN coding sequence was replaced with a fragment of DNA containing the coding sequence of the luciferase gene to obtain pBS-BAR-luc (see, above). After transfection of pBS-BAR-luc along with Tat and Rev expressing plasmids, intracellular levels of luciferase activity were measured. Results clearly indicated that a thousand-fold decrease in luciferase production was measured with pBS-BAR-luc plasmid with respect to the control plasmid 1LTR-luc-LTR-Circle in the presence of Tat and Rev expressing plasmids (Table 1). Interestingly, luciferase activity in the presence of pHXB2 was greatly increased in pBS-BAR-luc compared to 1LTR-luc-LTR-Circle transfected cells. These results clearly indicate that either the absence of a proper Kozak sequence or the inadequate functionality of IRES sequence affected luciferase and EDN translation.

TABLE 1

Luciferase Activity after transfection of pBS-BAR-luc in HeLa and HeLa-Tat Cells

| DNA | Luciferase Activity (RLU/µg protein) | | | | | |
|---|---|---|---|---|---|---|
| | HeLa | | | HeLa-Tat | | |
| Transfected | pRBK | Tat/Rev | pHXB2 | pRBK | Tat/Rev | pHXB2 |
| 1 LTR-luc-LTR-Circle | 1549 | 77996 | 86546 | 123241 | 82188 | 97865 |
| BS-BAR-luc | 9 | 89 | 696 | 10 | 72 | 3511 |
| pGEM-luc | 10 | 8 | 11 | 9 | 11 | 8 |

Inhibition of HIV-1 replication in cells expressing the protective gene.

The protective vectors were inserted into an episomal plasmid, pRBK, which serves two purposes: a) the plasmid does not require clonal selection and allows the analysis on a more representative bulk culture, and b) the plasmid does not disrupt the configuration of the transfected constructs which maintain their transcriptional structure (see FIG. 1). CEM T cells were stably transfected with either pRBK, pBAR or pBAR-EDN and analyzed for the presence of episomal DNA by Southern blot. The hybridization pattern from each culture showed that the episomal DNA was present as expected at day 0 before infection and remained unchanged at day 30 after infection with HIV-1$_{IIIB}$. CEM-RBK, CEM-BAR and CEM-EDN were infected with HIV-1$_{IIIB}$ at different estimated multiplicities of infection (MOI).

Reverse transcriptase (RT) activity and p24 release in the supernatants were measured to determine the production of HIV-1 over a 60 days period. Infection of the control CEM-RBK cells followed the typical course. Both RT and p24 were readily detected in CEM-RBK supernatants by seven days post infection, peaked at day fifteen and slowly decreased to reach minimum levels by day 60. This trend remained basically unchanged regardless of the MOI of infection. Similarly, the recovery of p24 and RT activity in the supernatant of the CEM-BAR cells indicated that these cells were productively infected by the HIV-1$_{IIIB}$. However, the detection of RT activity and p24 from the supernatant of CEM-BAR were slightly delayed when lower MOIs (0.2 and 0.02) were used for infection, indicating that the induction of delta-gag mutant had a partially protective activity in these cells. The absence of a steadily expressed delta-gag protein explains the absence of the stronger protective capability previously described in other systems (e.g., Lori, et al., *Gene Therapy*, 1, 27–31 (1994)). In contrast, infection of CEM-EDN was not productive, as demonstrated by the complete absence of RT activity and p24 in the supernatants of the infected cells over a period of 60 days. The inhibition of HIV-1 release from CEM-EDN cells was complete at any tested MOI. A primary field isolate was also tested in the same conditions. Inhibition of HIV-1 replication was complete in the CEM-EDN cells and only partial in CEM-BAR cells with respect to the CEM-RBK infected cells.

The amount of intracellular viral DNA was measured during the course of the infection using semi-quantitative PCR which detected the env region of the HIV-1. All the infected cultures were positive for HIV-1 at day 1 after the infection, indicating that the entry of HIV-1 into the infected cells was similar in either culture. In particular, infected CEM-RBK was strongly positive for HIV-1 DNA within the first days after infection, whereas in HIV-1 infected CEM-BAR cells a delay in the accumulation of HIV-1 DNA, which was more visible at lower MOI was detected, thus confirming the results obtained with viral p24 and RT activity in the supernatants. However, a dramatic inhibition of HIV-1 DNA production in CEM-EDN cells was observed as compared to both CEM-RBK and CEM-BAR cells. This inhibition appeared complete following the infection at lower MOI. These results indicated that all of the cultures were susceptible to infection with HIV-1, but while CEM-RBK and CEM-BAR permitted the spreading of the virus through the culture in a relatively short time, CEM-EDN suppressed the progression of the infection.

Extrachromosomal forms of HIV-1 are a measure of the replicating capability of the virus (Pauza, et al., *J. Exp. Med.*, 172, 1035–1042 (1990); Robinson, et al., *J. Virol.*, 64, 4836–4841 (1990)). In order to distinguish between integrated and unintegrated HIV-1 viral DNA forms, semiquantitative PCR was used to measure the amount of double LTR extrachromosomal forms of HIV-1 produced during the infection. The results of the experiment substantiated the findings obtained with env gene amplification. In comparison with the CEM-RBK control cells, HIV-1 replication was delayed in CEM-BAR cells and blocked in CEM-EDN. HIV-1 replication is not completely blocked in CEM-EDN cells, but rather is suppressed. Additionally, cell viability and surface CD4 in the infected CEM-EDN cells were high during the course of infection (over 90%).

The transcriptional activation of HIV-1 and protective genes during the course of the infection was determined by Northern blot analysis after infection of the transduced cells with HIV-1 at estimated MOI 2. HIV-1 RNA was readily detected at day 7 after the infection in CEM-RBK, CEM-BAR and CEM-EDN cells infected with HIV-1$_{IIIB}$, and detected at a lower level at day 3 after the infection. The pattern of HIV-1 RNA expression in the infected cells paralleled the recovery of RT activity and p24 in the supernatants. In particular, in the HIV-1 infected CEM-BAR cells, HIV-1 RNA production is delayed and lasts for a shorter period of time compared to CEM-RBK control cells. This is likely due to the activity of p55$_{delta-gag}$ produced by the 3.5 Kb mRNA detected below the singly spliced 4.0 Kb HIV-1 mRNA. In CEM-EDN cells, HIV-1 RNA was detected throughout the time course of analysis but, most importantly, the levels of expression were very low compared to both HIV-1 infected CEM-RBK and CEM-BAR cells. This is very likely due to the activity of EDN produced by the 4.0 Kb mRNA which co-migrates with the singly spliced 4.0 Kb HIV-1 mRNA. Taken together, these data indicate that EDN, although expressed at very low levels, inhibited HIV-1 replication at the transcriptional or post-transcriptional levels:

Vector Expressed RNA is Incorporated into the HIV-1 Virion.

Although no viral release was detected from CEM-EDN cells following infection with HIV-1, the vector was designed to contain all the required sequences which allow packaging of the RNA containing the protective gene into virions. To test the efficiency of such a mechanism, HeLa-Tat cells were co-transfected with the pHXB2 molecular clone of HIV-1 along with each of the plasmids, and pBAR was co-transfected with either a molecular clone of SIV-1 ($SIV_{mm251}$) or two different molecular clones of HIV-1 (pROD-1 and pSXb1). Forty-eight hours after transfections, supernatants were collected and the nature of the viral RNA extracted from the supernatants was determined by dot blot. Hybridization was carried out with a LTR probe, which recognizes both the HIV-1 genome and pBAR and pBAR-EDN produced RNA, or a EDN probe, which only recognizes pBAR-EDN produced RNA. Results demonstrated that the two genomes were packaged with comparable efficiency into the HIV-1 virion but less efficiently or not at all inside the HIV-2 and SIV-1 virions respectively. Reprobing the filter with the ampicillin gene was performed as a negative control to rule out any interference from the transfected DNA.

To determine whether the virions derived from cotransfection experiments were infectious, the supernatants from the transfected cells were used to infect PBLs and semi-quantitative PCR to detect pBAR-END RNA was performed. After amplification using primer pair EDNα/EDNω, full length unspliced pBAR-EDN RNA was clearly detectable 1 hour after the infection and the signal was reduced over the course of the experiment. The same RNA was amplified with a primer pair spanning the splice junction to detect the presence of the 0.8 kb mRNA derived from the splicing of the full length mRNA. PCR was positive at day 1 after the infection. This indicated that mRNA derived from the protective vector was transferred to other cells and likely reverse-transcribed and integrated, thus producing an mRNA which in the absence of Tat and Rev is fully spliced. Overall, these data demonstrated that pBAR-EDN derived mRNA was packaged in the presence of HIV:l and that the resulting virions infect CD4+ T cells, indicating that pBAR-EDN produced mRNA was integrated.

Example 2

Specific Variants of pBAR

FIG. 3 shows an alignment between pBAR, pBAR-ONC and pBAR-EDN (See, Example 1 for construction of plasmids). FIG. 4 shows details of pBAR-EDN, including the IRES sequence, the intervening sequence between IRES and the sequence for EDN, and EDN. FIG. 5 shows further constructs of similar design.

Constructs on the left have an optional deletion of the start codon of gag so that no Gag protein is translated from the nucleic acid which (except for the ATG start codon) otherwise encodes Gag. Inhibitors X and Y, where X and Y are independently selected from the inhibitors described herein, are produced. In one embodiment, the inhibitors are a dominant negative Rev protein and EDN. Typically, an antibiotic resistance allows for selection of transduced cells. On the bottom left, the RRE and INS elements are deleted from the Gag gene. The vector is used for the production of non-toxic genes such as antibodies. The antibodies bind, e.g., HIV or oncogene proteins, and transcription is initiated using Tat.

Constructs on the right are useful for cell transduction and gene therapy in general. While retaining the 5' LTR sequences needed for packaging in HIV based retroviral particles, the induction of the inhibitory genes is controlled by other promoters, such as CMV. In this case, Y is optionally EDN, X is optionally ONCONASE and CMV drives high levels of expression, which is cytotoxic to the cell. The vector is targeted, e.g., using a ligand-receptor targeted transfection system (see, e.g., Cotton et al. (1992) *Proc. Natl. Acad. Sci. USA* 89: 6094–6098). Similarly, tissue-specific expression is optionally conferred using a tissue specific promoter. For example, the probasin promoter is used to express inhibitory genes, e.g., in prostate cells. In another useful embodiment, the promoter is an inducible promoter such as a tetracycline-responsive promoter. In this embodiment, the inhibitors are produced in response to a specific external signal such as tetracycline.

Example 3

Block of HIV-1 Replication by HIV-1 Induced Expression of Eosinophil-Derived Neurotoxins in Jurkat cells and Demonstration of A Replication Block with Different HIV field Isolates To further demonstrate the general effectiveness of the anti-HIV constructs described, additional experiments showing inhibition of different field isolates of HIV-1 were performed. F the time course results of p24 recovery from the supernatant of CEM-RBK, CEM-BAR or CEM-EDN following infection with the primary field isolate $HIV\text{-}1_{BZ167}$ (left) or the molecular clone $HIV\text{-}1_{NL4\text{-}3}$ (right). Results indicate that the antiviral activity of EDN is exerted also on viral isolates in addition to $HIV\text{-}1_{IIIB}$ (described, e.g., in Example 1).

To further demonstrate the ability of the constructs to inhibit HIV in cells other than CEM T cells, the constructs were further tested for HIV inhibition in Jurkat T cells. FIG. 7 provides a time course showing a block of HIV-1 replication in Jurkat-EDN cells. Plasmids pRBK, pBAR, pBAR-EDN and pBAR-ONC were introduced by electroporation into Jurkat T cells (10 μg of DNA per $2.5\times10^7$ cells, 200 mV, 960 μF). Fourty eight hours after transfection, cells were cultured in RPMI medium with 10% fetal calf serum (FCS) and 800 μg/ml hygromycin B (Boheringer, Indianapolis, Ind.). For infections, cells were incubated with $HIV\text{-}1_{IIIB}$ at an estimated multiplicity of infection (m.o.i.) of 0.2. After 2 hours of incubation, cells were incubated in tissue culture flasks at a density of $0.5\times10^6$ per milliliter. Collection of the supernatants for viral p24 analysis was carried out on the indicated days. Results show that, with respect to the Jurkat-RBK control cell line, protection was complete in Jurkat-EDN cells, and partial in Jurkat-ONC and Jurkat-BAR cells. This indicates that the anti-HIV activity of EDN is effective in Jurkat cells, as well as for CEM cells.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill ill the art in light of the teachings of this invention that certain changes and modifications may be made thereto without departing from the spirit or scope of the appended claims.

What is claimed is:

1. An HIV-based cell transduction vector comprising a vector nucleic acid encoding:
   an HIV packaging site;
   a first viral inhibitor subsequence;
   a splice donor site;
   a splice acceptor site;
   an HIV Rev binding subsequence; and,
   a promoter subsequence;
   wherein:
   the first viral inhibitor subsequence is located between the splice donor site and the splice acceptor site;
   the splice donor site and the splice acceptor site permit splicing of the first viral inhibitor subsequence from the vector nucleic acid in the nucleus of a cell; and,
   the promoter subsequence is operably linked to the first viral inhibitor subsequence.

2. The cell transduction vector of claim 1, wherein the vector nucleic acid is translocated to the cytoplasm in the presence of an HIV Rev protein, and wherein splicing of the first viral inhibitor sequence is inhibited by Rev.

3. The cell transduction vector of claim 1, wherein the first viral inhibitor comprises a nucleic acid subsequence encoding a ribonuclease selected from the pancreatic RNAse A superfamily.

4. The cell transduction vector of claim 1, wherein the first viral inhibitor comprises a nucleic acid subsequence encoding a ribonuclease selected from the group of ribonucleases consisting of onconase from Rana pipiens occytes, and eosinophil-derived neurotoxin (EDN).

5. The cell transduction vector of claim 1, wherein the first viral inhibitor subsequence encodes a transdominant protein selected from the group of transdominant proteins consisting of transdominant Gag, transdominant Tat, and transdominant Rev.

6. The cell transduction vector of claim 1, wherein the vector further comprises a cell binding ligand selected from the group consisting of transferrin, c-kit ligand, an interleukin and a cytokine.

7. The cell transduction vector of claim 1, wherein the promoter is selected from the group of promoters consisting of a retroviral LTR promoter, a constitutive promoter, an inducible promoter, a tissue specific promoter, a CMV promoter, a probasin promoter and a tetracycline-responsive promoter.

8. The cell transduction vector of claim 1, wherein the vector further comprises an encephalomyocarditis virus internal ribosome entry site (IRES).

9. The cell transduction vector of claim 8, wherein the vector nucleic acid further encodes a second viral inhibitor, wherein expression of the second viral inhibitor is controlled by the IRES.

10. The cell transduction vector of claim 1, wherein the vector nucleic acid further encodes a second viral inhibitor.

11. The cell transduction vector of claim 1, wherein vector nucleic acid further encodes a multicistronic mRNA with a first open reading frame and a second open reading frame, which multicistronic mRNA comprises an IRES sequence which directs translation of the second open reading frame in a cell.

12. The cell transduction vector of claim 11, wherein the first open reading frame encodes a viral inhibitor.

13. The cell transduction vector of claim 1, wherein the vector comprises an HIV retroviral particle.

14. The cell transduction vector of claim 13, wherein the HIV retroviral particle is pseudotyped for transduction into hematopoietic stem cells.

15. The cell transduction vector of claim 1, wherein the vector nucleic acid is packaged into an HIV particle in a cell infected by a wild-type HIV.

16. The cell transduction vector of claim 1, wherein the vector nucleic acid is packaged in a liposome.

17. The cell transduction vector of claim 1, wherein the vector nucleic acid further encodes a reporter gene.

18. The cell transduction vector of claim 1, wherein the cell transduction vector is selected from the group of cell transduction vectors consisting of pBAR, pBAR-ONC, and pBAR-EDN.

19. The cell transduction vector of claim 1, wherein the viral inhibitor is an oncogene inhibitor.

20. The cell transduction vector of claim 1, wherein the vector further comprises a nucleic acid subsequence encoding an oncogene inhibitor.

21. The cell transduction vector of claim 20, wherein the oncogene inhibitor is a nucleic acid encoding an inhibitor selected from the group of inhibitors consisting of an antibody which specifically binds a Ras protein and an RNAse.

22. The cell transduction vector of claim 20, wherein the oncogene inhibitor is an RNAse from the RNAse A superfamily.

23. A cell transduction vector of claim 1, comprising a nucleic acid subsequence encoding a first viral inhibitor that is an EDN protein, which subsequence is operably linked to a promoter, wherein said cell transduction vector inhibits the replication of a retrovirus in a cell transduced by the cell transduction vector.

24. The cell transduction vector of claim 23, wherein the vector is pBAR-EDN.

25. The cell transduction vector of claim 23, wherein the cell is a CD4$^+$ cell.

26. The cell transduction vector of claim 23, wherein the cell is a stem cell.

27. The cell transduction vector of claim 23, wherein the vector inhibits the replication of HIV in the cell.

28. The cell transduction vector of claim 23, wherein the vector nucleic acid is packaged in a retroviral particle.

29. The cell transduction vector of claim 23, wherein the vector is packaged in a liposome.

30. The cell transduction vector of claim 23, wherein the vector further comprises a cell binding ligand selected from the group of cell binding ligands consisting of transferrin, kit-ligand, an interleukin, and a cytokine.

31. The cell transduction vector of claim 23, wherein the vector nucleic acid further encodes a subsequence encoding a retroviral chromosome integration subsequence.

32. The cell transduction vector of claim 23, wherein the vector further comprises a multicistronic mRNA which encodes a first open reading frame and a second open reading frame, which multicistronic mRNA is operably linked to a promoter, wherein the multicistronic mRNA comprises a subsequence encoding EDN.

33. The cell transduction vector of claim 23, wherein the promoter is selected from the group consisting of a tetracycline responsive promoter, a probasin promoter, and a CMV promoter.

34. A method of transducing a cell with a nucleic acid encoding a viral inhibitor comprising contacting the cell with the cell transduction vector of claim 1, wherein the cell is transduced in vitro.

35. An isolated cell comprising the cell transduction vector of claim 1.

36. The cell of claim 35, wherein the cell is selected from the group of cells consisting of CD4$^+$ cells, CD34$^+$ hematopoietic stem cells, and transferrin receptor$^+$cells.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 588 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 1..588
      (D) OTHER INFORMATION: /note= "encephalomyocarditis virus
         internal ribosome entry site (IRES)"

(xi) SEQUENCE DESCRIPTION: SEQ ID NO: 1:

```
ATTCCCCCCC TCTCCCTCCC CCCCCCCTAA CGTTACTGGC CGAAGCCGCT TGGAATAAGG     60

CCGGTGTGCG TTGTCTATAT GTTATTTTCC ACCATATTGC CGTCTTTTGG CAATGTGAGG    120

GCCCGGAAAC CTGGCCCTGT CTTCTTGACG AGCATTCCTA GGGGTCTTTC CCCTCTCGCC    180

AAAGGAATGC AAGGTCTGTT GAATGTCGTG AAGGAAGCAG TTCCTCTGGA YYCTTCTTGA    240

AGACAAACAA CGTCTGTAGC GACCCTTTGC AGGCAGCGGA ACCCCCCACC TGGCGACAGG    300

TGCCTCTGCG YYCAAAAGCC ACGTGTATAA GATACAGGTG CAAAGGCGGC ACAACCCCAG    360

TGCCACGTTG TGAGTTGGAT AGTTGTGGAA AGAGTCAAAT GGCTCTCCTC AAGCGTATTC    420

AACAAGGGGC TGAAGGATGC CCAGAAGGTA CCCCATTGTA TGGGATCTGA TTTGGGGCCT    480

CGGTGCACAT GCTTTACATG TGTTTAGTCG AGGTTAAAAA ACGTCTAGGC CCCCCGAACC    540

ACGGGGACGA GGTTTTTCCT TGAAAAACA CGATGATAAG CTTGCCAC                  588
```

(2) INFORMATION FOR SEQ ID NO: 2:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..44
      (D) OTHER INFORMATION: /note= "intervening sequence between
         IRES and EDN sequences in pBAR-EDN"

(xi) SEQUENCE DESCRIPTION: SEQ ID NO: 2:

```
CTAGAAATAA TTTTGTTTAA CTTTAAGAAG GAGATATACA TATG                      44
```

(2) INFORMATION FOR SEQ ID NO: 3:

(i) SEQUENCE CHARACTERISTICS:
      (A) LENGTH: 402 base pairs
      (B) TYPE: nucleic acid
      (C) STRANDEDNESS: single
      (D) TOPOLOGY: linear (ii) MOLECULE TYPE: DNA (genomic)

(ix) FEATURE:

(A) NAME/KEY: -
        (B) LOCATION: 1..402
        (D) OTHER INFORMATION: /note= "human eosinophil-derived
            neurotoxin (EDN) ribonuclease"

(xi) SEQUENCE DESCRIPTION: SEQ ID NO: 3:

AAACCGCCGC AGTTCACTTG GGCTCAGTGG TTCGAAACTC AGCATATCAA CATGACTTCT    60

CAGCAGTGCA CTAACGCTAT GCAGGTTATC AACAACTACC AGCGTCGTTG CAAAAACCAG   120

AACACTTTCC TGCTGACTAC TTTCGCTAAC GTTGTTAACG TTTGCGGTAA CCCGAACATG   180

ACTTGCCCGT CTAACAAAAC TCGTAAAAAC TGCCATCATT CTGGTTCTCA GGTTCCGCTG   240

ATCCATTGCA ACCTGACTAC TCCGTCTCCG CAGAACATCT CTAACTGCCG TTACGCTCAG   300

ACTCCGGCTA ACATGTTCTA CATCGTTGCT TGCGACAACC GTGACCAGCG TCGTGACCCG   360

CCGCAGTACC CGGTTGTTCC GGTTCATCTG GACCGTATCA TC                      402

(2) INFORMATION FOR SEQ ID NO: 4:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = Ser, Tyr or Thr"

(xi) SEQUENCE DESCRIPTION: SEQ ID NO: 4:

Met Lys Xaa Pro
1

(2) INFORMATION FOR SEQ ID NO: 5:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = Ser, Tyr or Thr"

(xi) SEQUENCE DESCRIPTION: SEQ ID NO: 5:

Met Lys Pro Xaa
1

(2) INFORMATION FOR SEQ ID NO: 6:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 3

```
                (D) OTHER INFORMATION: /product= "OTHER"
                    /note= "Xaa = Ser, Tyr or Thr"

(xi) SEQUENCE DESCRIPTION: SEQ ID NO: 6:

Met Asn Xaa Pro
1

(2) INFORMATION FOR SEQ ID NO: 7:

(i) SEQUENCE CHARACTERISTICS:
                (A) LENGTH: 4 amino acids
                (B) TYPE: amino acid
                (C) STRANDEDNESS: <Unknown>
                (D) TOPOLOGY: linear (ii) MOLECULE TYPE: peptide (ix) FEATURE:
                (A) NAME/KEY: Modified-site
                (B) LOCATION: 2
                (D) OTHER INFORMATION: /product= "OTHER"
                    /note= "Xaa = Ser, Tyr or Thr"

(xi) SEQUENCE DESCRIPTION: SEQ ID NO: 7:

Met Xaa Lys Pro
1

(2) INFORMATION FOR SEQ ID NO: 8:

(i) SEQUENCE CHARACTERISTICS:
                (A) LENGTH: 4 amino acids
                (B) TYPE: amino acid
                (C) STRANDEDNESS: <Unknown>
                (D) TOPOLOGY: linear (ii) MOLECULE TYPE: peptide (ix) FEATURE:
                (A) NAME/KEY: Modified-site
                (B) LOCATION: 2
                (D) OTHER INFORMATION: /product= "OTHER"
                    /note= "Xaa = Ser, Tyr or Thr"

(xi) SEQUENCE DESCRIPTION: SEQ ID NO: 8:

Met Xaa Pro Lys
1

(2) INFORMATION FOR SEQ ID NO: 9:

(i) SEQUENCE CHARACTERISTICS:
                (A) LENGTH: 35 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: -
                (B) LOCATION: 1..35
                (D) OTHER INFORMATION: /note= "oligonucleotide SU3"

(xi) SEQUENCE DESCRIPTION: SEQ ID NO: 9:

GCCTC CCGGGACTGG AAGGGCTAAT TCACT                                    35

(2) INFORMATION FOR SEQ ID NO: 10:

(i) SEQUENCE CHARACTERISTICS:
                (A) LENGTH: 29 base pairs
                (B) TYPE: nucleic acid
                (C) STRANDEDNESS: single
```

```
        (D) TOPOLOGY: linear (ii) MOLECULE TYPE: DNA (ix) FEATURE:
        (A) NAME/KEY: -
        (B) LOCATION: 1..29
        (D) OTHER INFORMATION: /note= "oligonucleotide EU5AS"

(xi) SEQUENCE DESCRIPTION: SEQ ID NO: 10:

ATTCA CCAGTCGCCG CCCCTCGCC                                            29

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..30
        (D) OTHER INFORMATION: /note= "oligonucleotide EU5S"

(xi) SEQUENCE DESCRIPTION: SEQ ID NO: 11:

ATTCG CCAAAAAATT TTGACTAGCG                                           30

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "oligonucleotide XDGAS"

(xi) SEQUENCE DESCRIPTION: SEQ ID NO: 12:

TAGAT CTAGATTGCC CCCCTATCAT TATTGT                                    36

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "oligonucleotide SRRES"

(xi) SEQUENCE DESCRIPTION: SEQ ID NO: 13:

CGTCG ACACCATTAG GAGTAGCACC CAC                                       33

(2) INFORMATION FOR SEQ ID NO: 14:

(i) SEQUENCE CHARACTERISTICS:
        (A) LENGTH: 29 base pairs
        (B) TYPE: nucleic acid
```

```
        (C) STRANDEDNESS: single
        (D) TOPOLOGY: linear (ii) MOLECULE TYPE: DNA (ix) FEATURE:
        (A) NAME/KEY: -
        (B) LOCATION: 1..29
        (D) OTHER INFORMATION: /note= "oligonucleotide BLU5AS"

(xi) SEQUENCE DESCRIPTION: SEQ ID NO: 14:

ATCCA CTGACTAAAA GGGTCTGAG                                          29

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..23
        (D) OTHER INFORMATION: /note= "oligonucleotide ENVA"

(xi) SEQUENCE DESCRIPTION: SEQ ID NO: 15:

TATCA GCACTTGTGG AGA                                                23

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "oligonucleotide ENVB"

(xi) SEQUENCE DESCRIPTION: SEQ ID NO: 16:

GGCCC AAACATTATG TACCT                                              25

(2) INFORMATION FOR SEQ ID NO: 17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "oligonucleotide ENVC"

(xi) SEQUENCE DESCRIPTION: SEQ ID NO: 17:

CTCTA TTTTGTGCAT CAGATG                                             26

(2) INFORMATION FOR SEQ ID NO: 18:

(i) SEQUENCE CHARACTERISTICS:
        (A) LENGTH: 23 base pairs
```

(B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..23
        (D) OTHER INFORMATION: /note= "oligonucleotide IRESA"

(xi) SEQUENCE DESCRIPTION: SEQ ID NO: 18:

AGAGG AATTCCGCCC CTC                                                    23

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "oligonucleotide IRESB"

(xi) SEQUENCE DESCRIPTION: SEQ ID NO: 19:

GTGGC AAGCTTATCA TCGTG                                                  25

(2) INFORMATION FOR SEQ ID NO: 20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..32
        (D) OTHER INFORMATION: /note= "oligonucleotide EDNalpha"

(xi) SEQUENCE DESCRIPTION: SEQ ID NO: 20:

ATCCT TGATATGCTG AGTTTCGAAC CA                                          32

(2) INFORMATION FOR SEQ ID NO: 21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..40
        (D) OTHER INFORMATION: /note= "oligonucleotide EDNomega"

(xi) SEQUENCE DESCRIPTION: SEQ ID NO: 21:

AAAAA GCGGCCGCCT ACTAGATGAT ACGGTCCAGA                                  40

(2) INFORMATION FOR SEQ ID NO: 22:

(i) SEQUENCE CHARACTERISTICS:

```
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "oligonucleotide ECOSPL"

(xi) SEQUENCE DESCRIPTION: SEQ ID NO: 22:

GCGAC TGGTGAATT                                                     19

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "oligonucleotide OTESAPL"

(xi) SEQUENCE DESCRIPTION: SEQ ID NO: 23:

CACTT CTCTCTCCGG GT                                                 22
```